United States Patent [19]

Bohannan et al.

[11] Patent Number: 4,901,575
[45] Date of Patent: Feb. 20, 1990

[54] METHODS AND APPARATUS FOR MONITORING STRUCTURAL MEMBERS SUBJECT TO TRANSIENT LOADS

[75] Inventors: William L. Bohannan, Gales Ferry; J. Vincent Harrington, Groton, both of Conn.; John K. Pfister, Mt. Airy, Md.

[73] Assignee: GP Taurio, Inc., Columbia, Md.

[21] Appl. No.: 278,196

[22] Filed: Nov. 30, 1988

[51] Int. Cl.⁴ .......................................... G01D 21/00
[52] U.S. Cl. .......................................... 73/587; 73/594
[58] Field of Search ................. 73/587, 594, 579, 583, 73/584, 801; 364/507

[56] References Cited

U.S. PATENT DOCUMENTS

| | | | |
|---|---|---|---|
| 2,668,444 | 2/1954 | Berman | 73/88 |
| 3,744,300 | 7/1973 | Fleury | 73/67.3 |
| 3,875,381 | 4/1975 | Wingfield et al. | 73/587 X |
| 3,956,926 | 5/1976 | Phillips | 73/152 |
| 4,164,149 | 8/1979 | Okubo | 73/594 |
| 4,188,830 | 2/1980 | Mason et al. | 73/801 |
| 4,397,186 | 8/1983 | Phelan et al. | 73/584 |
| 4,429,578 | 2/1984 | Darrel et al. | 73/660 X |
| 4,481,818 | 11/1984 | Hellqvist | 73/587 |
| 4,535,629 | 8/1985 | Prine | 73/587 |
| 4,549,437 | 10/1985 | Weins et al. | 73/587 |
| 4,550,604 | 11/1985 | Sugimoto et al. | 73/660 X |
| 4,559,828 | 12/1985 | Liszka | 73/660 X |
| 4,561,062 | 12/1985 | Mitchell | 364/555 |
| 4,598,592 | 7/1986 | McMaster | 73/786 |
| 4,609,994 | 9/1986 | Bassim et al. | 364/551 |

OTHER PUBLICATIONS

K. S. Fu, Ed., Pattern Recognition & Machine Learning (Plenum Press, 1971), pp. 1-3, 127-129.
Seven Pages of Abstracts, non-patent publications.
Eight pages of Abstracts, patent publications.
G. P. Taurio, Inc., Bridge Structural Testing and Monitoring.
La Shomb, Bridge Vibration, (University of Connecticut 1985).
Structural Testing, Part 1 Mechanical Mobility Measurements and Part 2 Model Analysis and Simulation (Bruel & Kjaer).

Primary Examiner—Jerry W. Myracle
Attorney, Agent, or Firm—Irene J. Frangos; Robert M. Isackson

[57] ABSTRACT

A method and apparatus for monitoring the structural acoustic signature of a structural member in response to a transient load, corresponding to detected vibration frequencies transmitted by the structural member including the fundamental and harmonic frequencies of the structural member, to determine changes in structural integrity and to determine the nature and type of transient loads. The structural acoustic signature of the structural member in a first condition in response to a first transient load is compared to a structural acoustic signature from a second transient load whereby differences in the signatures correspond to the occurrence of changes in the elastic qualities or condition of the structural member. The signatures are preferably evaluated in the frequency domain. The nature and type of transient load can be determined by evaluating the waveform shape of a structural member in response to the unknown load against a history of waveform shapes corresponding to known laods. A plurality of remote structural members such as highway bridges may be monitored by a central station.

35 Claims, 9 Drawing Sheets

VELOCITY / LOAD
            SLOW                    FAST
LIGHT       
        FIG. 2(a)           FIG. 2(b)
MEDIUM   
        FIG. 2(c)           FIG. 2(d)
HEAVY   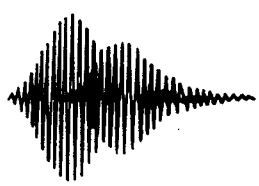
        FIG. 2(e)           FIG. 2(f)
VERY HEAVY 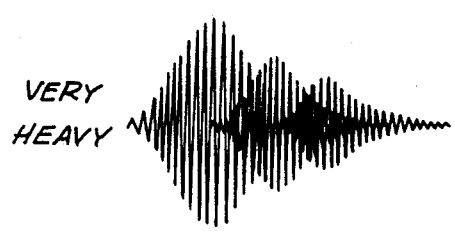  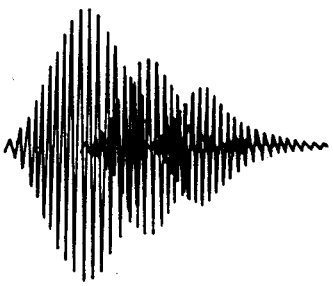
        FIG. 2(g)           FIG. 2(h)

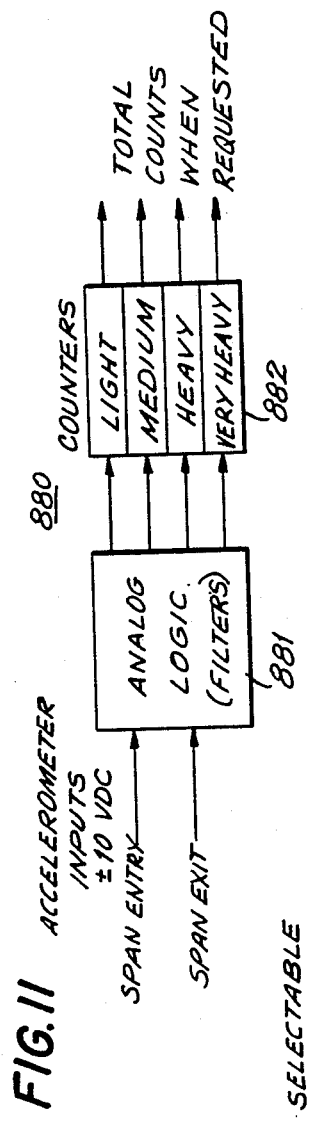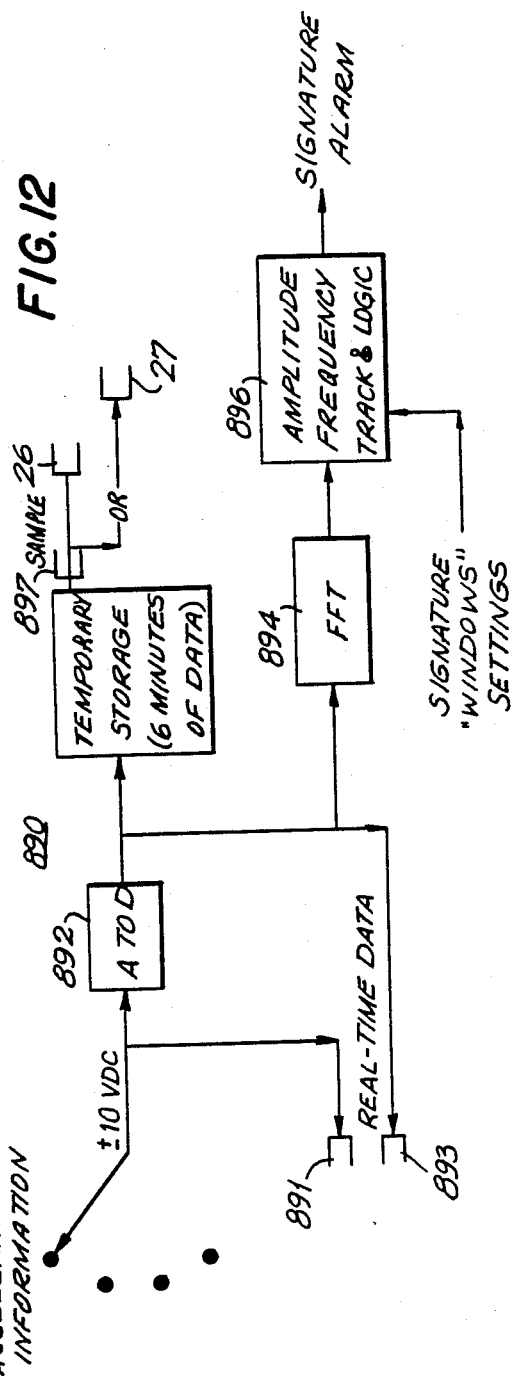

METHODS AND APPARATUS FOR MONITORING STRUCTURAL MEMBERS SUBJECT TO TRANSIENT LOADS

BACKGROUND OF THE INVENTION

This invention relates to methods and apparatus for monitoring structural members subjected to transient loads, more particularly, to monitoring and analyzing the frequency characteristics of a structural member vibrating in response to a transient load in order to measure changes in the structural integrity of the member and to classify transient loads by nature and type.

As used herein, the following terms are defined in a conventional manner "acoustic" means relating to sound; "sound" means a vibratory disturbance in the pressure and density of a fluid or in the elastic strain in a solid; "vibration" means oscillation of a parameter (e.g., displacement, velocity, acceleration) that defines the motion of a mechanical system; "sonic" means sound with a frequency in the audible range of the human ear, between about 20 and 20,000 Hz.; "ultrasonic" means sound with a frequency above the audible range of the human ear; "infrasonic" means sound with a frequency below the audible range of the human ear; and "waveform" means the instantaneous amplitude of a signal as a function of time.

As used herein, a "structural member" is defined as a mass of material having an elasticity that is capable of transmitting sounds, including standing waves, corresponding to vibratory motion of the structural member in a direction along a selected dimension of the mass. A structural member is further defined as a mass that is acoustically isolated from adjacent structural elements sufficiently so that the sounds corresponding to the motion of the structural member can be discriminated from the sounds corresponding to the motion of other structural elements. Typically, a structural member has six dimensions of motion; three orthogonal translational dimensions—e.g., horizontal, vertical, and lateral—and three rotational dimensions—one dimension of rotation about each translational dimension.

As used herein, a "transient load" is defined as a stress-event caused by the application of a force (mass) to a structural member for a duration of time and which stimulates on the structural member to vibrate, thereby to transmit sounds corresponding to the impact of the transient load. A transient load may be applied to one or more specific locations on the structural member, or to the entire structural member.

Structural members are used in construction and have a certain load bearing capability that is related to the size, elasticity and yield strength of the member, which determine how much displacement or deflection the member can withstand without permanent deformation or other irreversible change in mechanical properties.

Structures exposed to repeated transient loads of the same or differing magnitude or duration, or are susceptible to defects caused by fatigue of the materials used, which defects affect adversely the load bearing capabilities, i.e., the structural integrity, of the structural member. Such defects may be localized structural defects such as cracks and fatigue fractures. Similarly, structures which are exposed to weather over extended periods of time are subject to defects caused by corrosion or oxidation, or general changes to the mass or its microstructure resulting from, for example, defective materials, defective materials processing or manufacturing techniques, excessive stress events over use, and the like. Significant defects can result ultimately in complete structural failure of the member even when it is subjected to a transient load that is within the original load bearing capability of the structural member. Accordingly, structural members are periodically inspected in an effort to discover any defects that might affect the structural integrity before a structure becomes unsafe for its intended purpose, so that the member can be repaired, replaced or taken out of service.

Highway and railway bridges are examples of structures composed of structural members that are subject to transient loading and exposed to the elements where failure of a structural member can have catastrophic consequences. There are approximately 600,000 bridges throughout the United States of widely differing age and condition. Many of these bridges are composed of multiple spans, where each span is supported by one or more support beams.

The number of bridge inspectors in many places is too few to inspect adequately all of these structures and their component structural members for safety and the degree of use (which affects expected life) at sufficiently frequent intervals. Furthermore, in many instances, visual inspections and conventional diagnostic measurements alone are inadequate to evaluate the safety of the structure, particularly to detect reliably fatigue cracks, fractures, corrosion or oxidation or other defects that are invisible to the human eye.

Heretofore, methods of monitoring structural members for defects and undesired changes in structural integrity and for safety inspection purposes have depended largely upon visual inspection, destructive testing, i.e., testing the load carrying ability of the design to failure and extrapolating the test results to a structure in actual use, and non-destructive testing, i.e., testing structural integrity of the member without destroying its functional utility. Non-destructive testing techniques include using ultrasonic stimulators to produce ultrasonic signals in the structure at frequencies of from about 100 kHz to about 500 kHz which can be used to detect defects, e.g., U.S. Pat. Nos. 4,598,592, 4,535,629, 4,397,186 and 4,188,830, using magnetic eddy current flow to detect anomalies in the magnetic field caused by physical defects in a structure, transmitting mechanical acoustic vibrations at a point on the structure surface to produce mechanical vibration reasonances that may be detected by a microphone, and by performing stress measurements by x-ray diffractometry, e.g., U.S. Pat. No. 4,561,062.

U.S. Pat. No. 4,609,994 refers to monitoring acoustical emissions of a structure placed under stress using a detector-analyzer unit wherein the detector is an acoustic transducer secured to each structural member for providing an output signal representative of any acoustic emission, e.g., a piezoelectric transducer at frequencies of from 0.1 to 2 mHz or an accelerometer transducer at frequencies of from 1 to 20 kHz, and the analyzer is at least one signal conditioner circuit coupled to the transducer output signal for providing at least one derivative signal having characteristics correlatable with preselected characteristics of the output signal of the acoustic detector, a measuring circuit coupled to the signal conditioner circuit providing, for each derivative signal, a digital output signal representing one of a set of emission parameters correlatable with the preselected characteristics of the output signal of the detector, and a microprocessor coupled to each measuring circuit that contains a set of base values for periodically comparing the set of base values with corresponding detecting emission parameters to determine the existence of a problem situation when base values are exceeded. The microprocessor is connected to the central control unit which receives warning signals and other data from a plurality of remote detector-analyzer units associated with a plurality of structures and is the center for coordinating a suitable response. The central control unit also can program and reprogram the remote detector-analyzer units.

U.S. Pat. No. 4,164,149 refers to using angular motion sensors including an electrically conductive element and a permanent magnet secured to a structure so that angular deflection of the structure will cause relative movement of the coil and magnet and cause a current to flow. A plurality of angular motion sensors can be located at selected locations of a composite structure to obtain an initial waveform signature of the composite structure and a ratio of the input signals causing the vibration to the measured angular deflection signals, can be obtained by comparing the amplitude, phase, and frequency characteristics typically using fast Fourier transform techniques, so that subsequent changes to the initial composite waveform signature, which indicate corresponding changes in the structural characteristics of one or more individual components can be determined.

U.S. Pat. No. 4,549,437 refers to providing each segment of a complex multiple segment structure with at least one acoustic sensor, recording the intensity and frequency distirbution of the sensed acoustic waves, and comparing the sensed acoustic waves against either a standard or over time and/or from one segment to another segment of the complex structure. Acoustic sensors are described as piezoelectric sensors and frequencies below 100 kHz are filtered to be removed from the signal.

These techniques, however, have been of limited use in many structures because of their inherent complexity and expense in implementation, the labor intensive procedures of interrogating a structure and interpreting the results of the interrogation, and because their use is typically limited to structures of certain material compositions and cannot be broadly applied to support members of different compositions such as concrete.

Predicting the structural health of a structure also is limited by the known methods of determining the nature and type of transient loading on structures. For example, in the case of bridges, these latter methods include using persons to take infrequent surveys of the type and volume of traffic, using pneumatic tubes across roadways to count vehicles, using radar to determine the speed of vehicles, and weighing selected vehicles to develop vehicle-weight profiles to estimate the use and loading on a road or bridge. These techniques, while often useful, suffer from the necessity of having to imply results based upon analyses or computer models or the loads being experienced by the structure and are subject to error because they utilize a small sample of selected vehicle-weight data that may or may not correspond to actual usage of the particular structure. Further, the equipment used to obtain the information is subject to vandalism or damage during data acquisition and require substantial operator supervision to obtain usable data. Additionally, the existing methodology also fails to take into account factors which are known to have a significant effect on vehicle affects on a bridge, including, without limitation, the type of suspension of the vehicle and discontinuities in the bridge surface, e.g., potholes, bumps, debris, etc.

Considerable effort has been devoted to measuring and modeling the dynamic behavior of bridges or bridge components in response to transient loads imposed by vehicular traffic to aid in the determination of safe loading capabilities and to the design of safer bridges. Techniques for measuring the sound transmitted by and the sound generated by support beams of bridge spans of various types and under various conditions, are known. Strain gauges, deflectometers, accelerometers, and seismometers have been used in various combinations to detect stress, deflection or displacement, and acceleration of bridge support beams. Techniques for using microphones and other acoustic emission sensors to detect sounds generated by bridges either in response to an applied mechanical or acoustical force, or self-generated in response to a transient load, also are known.

A bridge span support member will respond to a passing vehicle by vibrating. The resulting sounds Will be transmitted along its various dimensions. While the vehicle is on the support member, the member will vibrate at a fundamental and harmonic frequencies in accordance With the forced function of the combined mass of the structural member and the vehicle. After the vehicle has left the bridge, the support member will continue to vibrate at the natural fundamental and harmonic frequencies of the support member. These vibrations along a given direction or dimension thus form a characteristic structural acoustic signature of the member in the given direction in response to a variety of transient loads.

As used herein, the term "structural acoustic signature" means the variation, over time, of selected frequency amplitude peaks of the spectral plot of a structural member vibrating in its free mode, i.e., vibrations which occur subsequent to the transient load that stimulated the vibrations in a given dimension. The spectral plot is mathematically derived from the detected sound signals in the given dimension by performing a fast Fourier transform ("FFT") upon a sample of detected sound signals transmitted by or other vibrational information of the structural member being monitored.

The vibrational information is typically detected by accelerometers placed on the structural member to detect sonic and infrasonic frequencies. Different dimensions will have different lengths, and, hence, different natural frequencies and structural acoustic signatures, accordingly. Thus, a structural member may have a composite signature including more than one structural acoustic signature in more than one dismension.

It also is known from the bridge vibration studies that (1) the speed of a vehicle passing over a span affects the vibration pattern; usually the peak amplitude of vibration dynamic of motion increases with increasing vehicular speed, (2) the amplitude of the forced vibration also is a function of the impact of the vehicle, (3) the roughness of the approach to the bridge appears to affect the oscillations of the bridge more than the roughness of the surface of the bridge. It also i known that the suspension system and the number of axles and the spacing between axles of the vehicles and the axle and vehicle frequencies affect the nature of the motion of the bridge, and that when the natural resonant frequency of the axle or the vehicles is the same as that of the bridge, there is resonance resulting in increased amplitude of vibration of the bridge.

Notwithstanding years of development effort and study and the need for improved monitoring of and enhanced inspection techniques for determining the safety of structural members, including without limitation bridges, there is no commercial use of a method or apparatus for monitoring structural members subjected to transient loads that provides directly measured information regarding changes in the relative structural integrity and/or the nature of the transient loading of the structure having the advantages and benefits of the present invention.

It is, therefore, an object of this invention to provide direct measurement of changes in the structural integrity of a structural member. It is a further object to measure changes in the structural acoustic signature of a structural member in response to a transient load to identify changes in the structural integrity of the structural member. It is another object to obtain more than one independent measurement of the structural responses and to correlate the independent measurements, thereby to obtain enhanced determinations of any changes. It is a further object to measure such changes using transient loads that are normally applied to the structural member being monitored during use.

It is another object of the invention to measure changes in stiffness of the structural member based on changes in the structural acoustic signature of the member in response to transient loads.

It is another object of the invention to provide for monitoring structural members of bridge spans using sensors for detecting the sound transmitted by the structural member in response to a transient load in one or more dimensions and particularly using accelerometer sensor systems to detect sonic and infrasonic sounds.

It is another object of the invention to provide for analyzing the detected sounds to count the number of transient loads acting on the member.

It is another object of the invention to provide for analyzing the detected sounds to determine the duration and, hence, velocity of a transient load.

It is another object of the invention to provide for analyzing the detected sounds to determine the mass of a transient load.

It is a further object of the invention to measure and record the number of stress range events on a structural member to provide a history for fatigue calculations.

It is another object to identify and classify transient loads applied to structural members by accumulating counts of vibration waveforms corresponding to the motion of the support member as it is stimulated by a given transient load including the onset, the maximum deflection, and the withdrawal of the transient load, and after the withdrawal of the load, whereby vibration waveforms of unknown transient loads can be identified by comparision of one or more components of the unknown waveforms to a library of waveforms of known transient loads or to a plurality of threshold signals establishing the different categories of possible transient loads and identifying a category corresponding to the transient load.

It is a further object of this invention, in the context of highway bridges, to provide for identifying, counting, weighing, and determining the speed of moving vehicles crossing a structural member supporting a bridge span using accelerometer sensors and/or seismic accelerometer sensors for detecting sonic and infrasonic sounds.

It is a further object of this invention to provide an automated central station monitoring system for monitoring a plurality of remote structural members for change in their structural integrity and the nature and type of transient loading without requiring continuous operator supervision at the central monitoring station.

SUMMARY OF THE INVENTION

The present invention provides for methods and apparatus for monitoring structural members subjected to transient loads over time to identify and/or measure changes in the structural integrity of the structural member and, separately, to obtain information regarding the nature and frequency of the transient loading on the structural member.

This invention provides for measuring changes in the structural integrity of a structural member by detecting changes in the sounds transmitted by the structural member in response to transient loads occurring at different times, which changes are unrelated to changes in weather or the environment of the structural member. Changes in the structural integrity as a result of localized defects such as, but not limited to, fatigue fractures, cracks, and crystalization, alter the sound transmission characteristics and, hence, the structural acoustic signature of the structural member. These changes are manifested by changes to, or the existence of additional frequencies or amplitudes appearing in the structural acoustic signature. These changes are readily identifiable and detectable by comparing structural acoustic signatures of the structural member prior to and subsequent to the defect.

Changes in the structural integrity as a result of defects that affect the entire structure such as, but not limited to, a change in elasticity or stiffness of the structural member due to repeated transient loading during use, or corrosion from continued exposure to the environment, also alter the sound transmission characteristics and, hence, the determined structural acoustic signature of the structural member. These changes are manifested by a shifting of the characteristics of the structural acoustic signature by more than a predetermined amount over time. The predetermined amount is selected to include changes in the signatures which result from changes in ambient weather conditions or other environmental changes that may occur between the detected signatures being compared, and to allow for a margin of tolerance.

Accordingly, by detecting structural acoustic signatures of a structural member in response to transient loads at different times and identifying changes to the frequencies or amplitudes of these signatures, changes in structural integrity can be identified and any appropriate corrective action can be taken.

It also has been discovered that a detected vibration waveform as a result of an unknown transient load can be analyzed to determine certain characteristics of the transient load used to excite the structural member. A detected waveform may be evaluated by examining selected characteristics, or in its entirety. In this regard, a structural member can be identified in terms of a detected waveform including the natural fundamental and harmonic sound frequencies of the member, e.g., subsequent to a transient load. Thereafter, the detected waveform can be analyzed and categorized by the detected fundamental and harmonic frequencies of the forced function of the combined mass of the structural member and the applied load during the transient load, and the natural fundamental and harmonic sound frequencies subsequent to the transient load, including, the number of harmonic frequencies and the amplitudes of the respective detected frequencies.

The categorization may be accomplished by selecting a plurality of threshold signals corresponding to the boundaries of each desired category of each parameter to be evaluated and comparing the detected waveform to the thresholds to determine in which category the detected waveform belongs. Alternately, the categorization may be accomplished by providing a library containing the detected waveforms of the structural member in response to a plurality of known transient loads covering the range of transients expected whereby the the waveform of the member in response to an unknown transient load can be evaluated and compared to the accumulated waveforms in the library to determine the characteristics or parameters of the unknown transient by the closest match to a waveform in the library. The accuracy of the determination may be controlled by the number of threshold ranges specified or the size of the library, and the desired precision of the evaluation. Optionally, interpolation techniques may be used to provide estimates based on closest matching threshold or waveform data.

In the preferred embodiment, the detected sounds transmitted by the structural member in a given dimension are converted from the time domain into the frequency domain, using Fourier analysis techniques, more preferably, fast Fourier transform techniques, to obtain a structural acoustic signature including the spectral lines of the sounds and their respective amplitudes of the detected frequencies detected at different times. The detectable range of sound frequencies depends upon the size of the structural member in the selected dimensions to be monitored and the likely number of harmonic frequencies that can be excited by the range of transient loads likely to impact the structure.

In the context of structural members that are bridge span support beams, the transient loads may be vehicles traveling the longitudinal length of the span, for example, cars, trucks, and busses of different sizes and weights and at different speeds. In this embodiment, the duration of the transient load is related to the speed of the vehicle and the length of the span.

In another embodiment, the present invention is adapted to monitor a structural member that is a radio antenna tower or a structural component of a radio tower, and the transient loads may be gusts of wind or earthquakes.

In another embodiment, the present invention is adapted to monitor a structural member that is an oil platform or a structural component of an oil platform and the transient load may be ocean swells, oil pressure in active wells, drilling pressures, wind, earthquakes, and the like.

In another embodiment, the present invention is adapated to monitor a structural member that is a support beam in a building.

In all of these and other embodiments, a transient load also may be imposed by mechanically, electromechanically, or acoustically stimulating the structural member to cause the member to vibrate and transmit sound. However, it is preferred to use transient loads that normally impinge on the structure during normal use.

BRIEF DESCRIPTION OF THE DRAWINGS

Further features of the invention, its nature and various advantages will be more apparent from the accompanying drawings and the following detailed description of the invention in which like reference numerals refer to like elements, and in which:

FIG. 2a is an illustrative plot of a waveform generated by a structural member in response to a transient load of first mass and velocity;

FIG. 2b is an illustrative plot of a waveform generated by a structural member in response to a transient load of a first mass and second velocity;

FIG. 2c is an illustrative plot of a waveform generated by a structural member in response to a transient load of a second mass and first velocity;

FIG. 2d is an illustrative plot of a waveform generated by a structural member in response to a transient load of a second mass and second velocity;

FIG. 2e is an illustrative plot of a waveform generated by a structural member in response to a transient load of a third mass and first velocity;

FIG. 2f is an illustrative plot of a waveform generated by a structural member in response to a transient load of a third mass at the second velocity;

FIG. 2g is an illustrative plot of a waveform generated by a structural member in response to a transient load of fourth mass and first velocity;

FIG. 2h is an illustrative plot of a waveform generated by a structural member in response to a transient load of fourth mass and second velocity;

FIG. 11 is a block diagram for determining the count and categorization of transient loads on a structural member in accordance with the present invention;

FIG. 12 is a block diagram for analyzing structural acoustic signatures of a structural member in response to transient loads in accordance with the present invention.

DETAILED DESCRIPTION OF THE INVENTION

Figure 1:
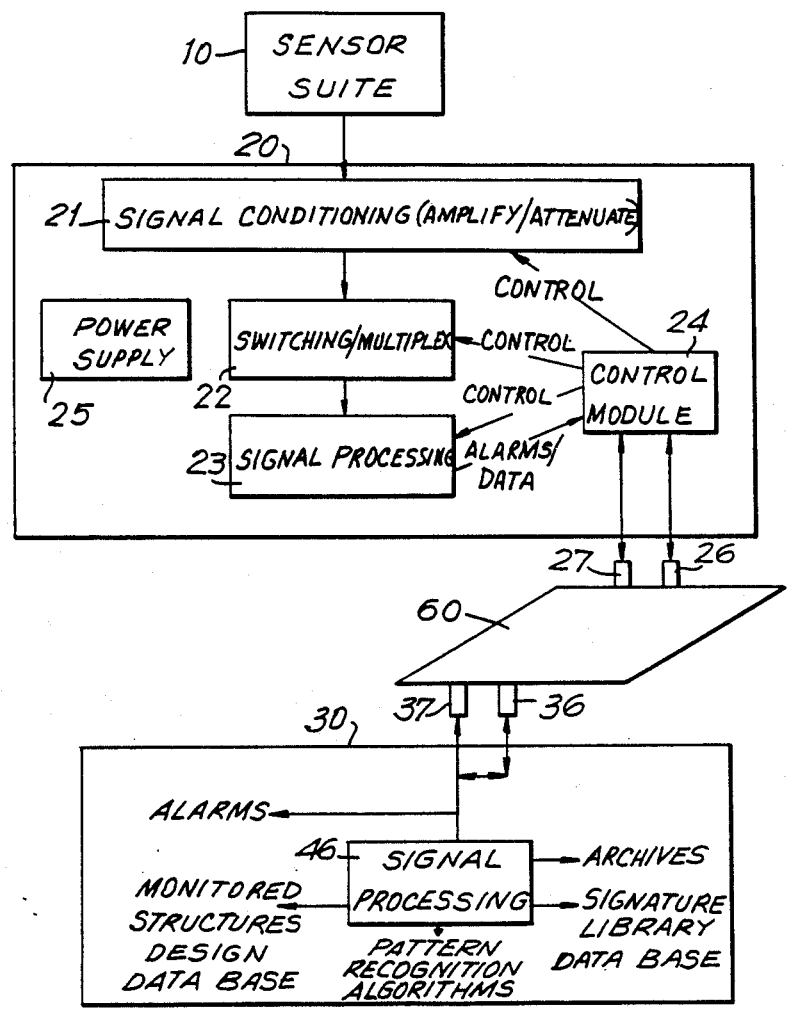
FIG. 1 is a block diagram of the apparatus for monitoring a structural member in accordance with an embodiment of the present invention.

Referring to FIG. 1, the apparatus of one embodiment of the present invention includes sensor 10, electronics unit 20, optionally, communications network 60, and central monitoring station 30.

Sensor 10 is a device capable of detecting the sounds present in the structural member, preferably by the vibrations associated with the motion of the structural member being monitored, from which a waveform specific to the structural member can be determined. Sensor 10 preferably detects motion along one dimension of the structural member at a time. More preferably, sensor 10 is a device for measuring acceleration of the structural member as and after it is subjected to a transient load. Sensor 10 also may measure displacement of the structural member, either directly, or by integration of the measured acceleration information.

Conventional accelerometers or seismic accelerometers having a bandwidth and frequency response sufficient to detect the sound frequencies of interest are useful as sensor 10. The frequencies of interest are based upon the dimensions of the structural member and the possible fundamental and harmonic frequencies that can be supported along the selected dimension. For example, to detect frequencies beween 0.7 Hz and 6 kHz, an accelerometer such as Model 308B03, manufactured by PCB Piezotronics, Inc., Depew, New York, may be used. These frequencies correspond to a structural member having a length of from about 2.5 to about 21,000 feet in the dimension of interest.

Sensor 10 is adapted to be securely attached to the structural member to be monitored, preferably permanently. Attachment may be by welds, welded studs, bolts, adhesives, magnets, or the like. Using a detachable connection permits using the same sensor to obtain measurements on several structural members which may be useful when continuous monitoring of an element is not desired.

Sensor 10 may further comprise a plurality of separate sensors for detecting the sounds in the same structural member at about the same location along different dimensions. For example, a plurality of accelerometer devices may be used, oriented at right angles to each other, such as a conventional triaxial accelerometer device, e.g., Model Nos. 307A or 306A06 manufactured by PCB Piezotronics, Inc.

Figure 4:
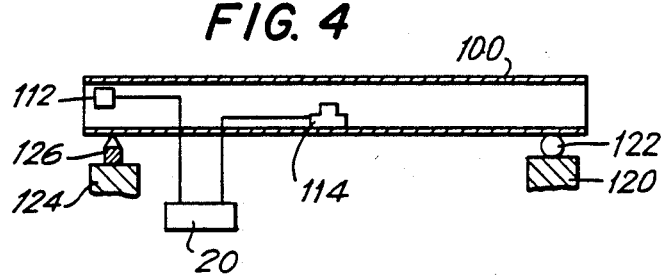
FIG. 4 is a schematic representation of a configuration to monitor displacement and elasticity changes of an embodiment of the invention.

Referring to FIG. 4, sensor 10 also may include accelerometer 112, preferably a triaxial accelerometer, and accelerometer 114, preferably a seismic accelerometer for measuring the acoustic waves transmitted by the same structural member in more than one dimension at different locations on that member simultaneously. A typical seismic accelerometer is Model No. 393C, manufactured by PCB Piezotronics, Inc., having a frequency range of from 0.01 Hz to about 1200 Hz. A plurality of sensors located at different positions also could be used.

Figure 6:
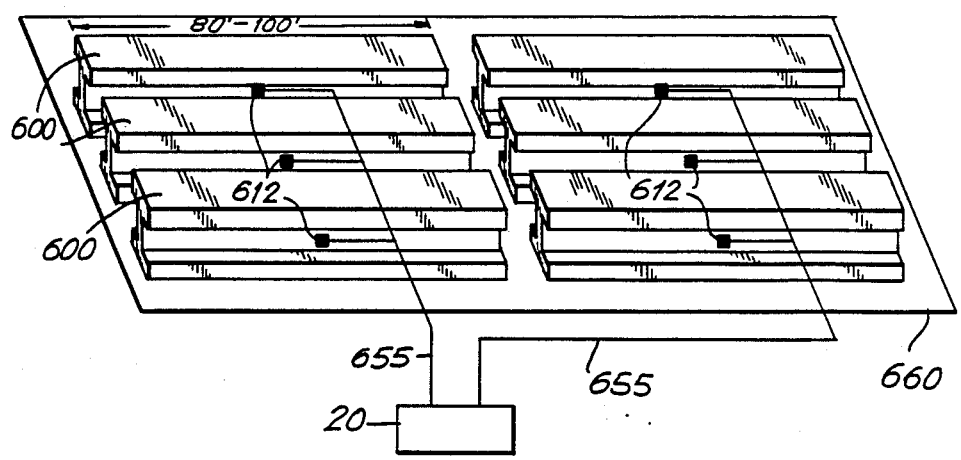
FIG. 6 is a partial sectional perspective view of a bridge showing two span lengths and a transducer configuration for such spans of an embodiment of the invention.

Referring to FIG. 6, sensor 10 also may comprise a plurality of sensors 612 whereby each sensor measures the response of a different structural member in one or more dimensions of each member. Further, sensor 10 may include a microphone or other esonic transducer device (not shown) to detect sound self-generated by the structural member in response to a transient load so that unusual sounds may be use to evaluate the relative condition of the structural member, or a clinometer transducer for detecting the tilt of a structural member.

Figure 8:
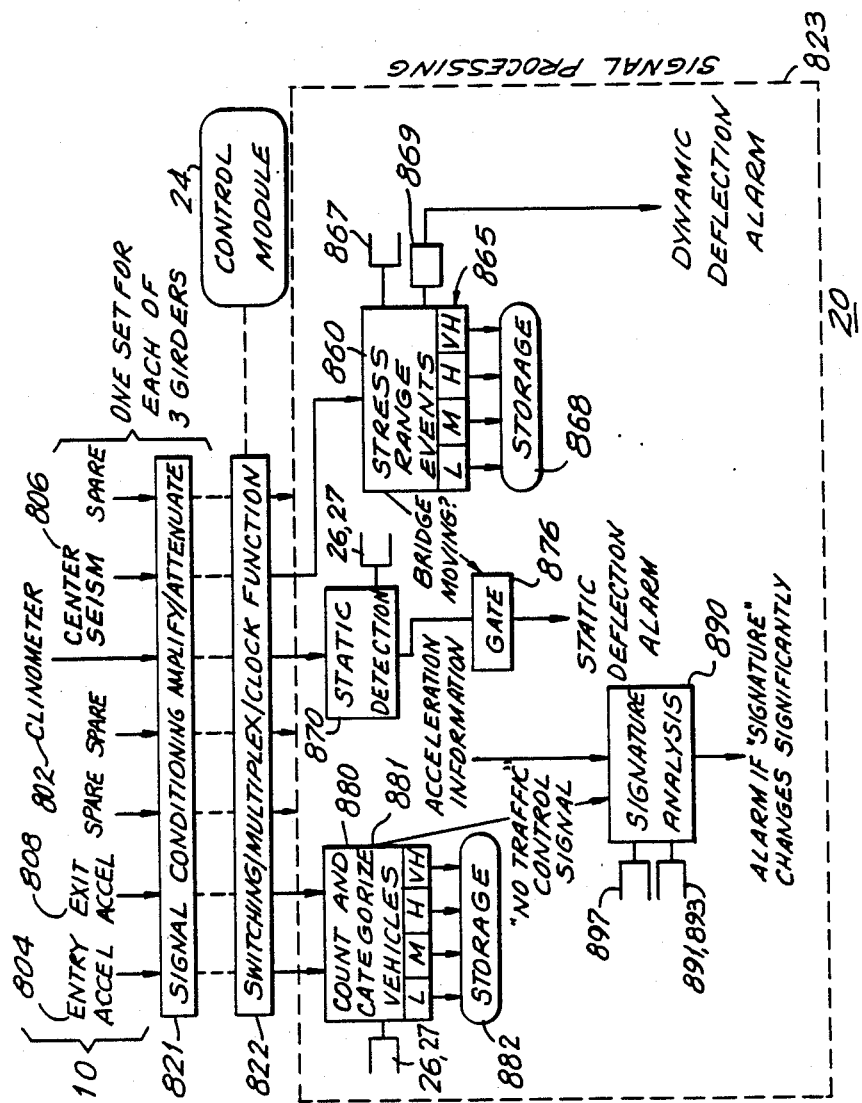
FIG. 8 is a block diagram of the apparatus for central station monitoring of structural members in accordance with an embodiment of the present invention.
Figure 13:
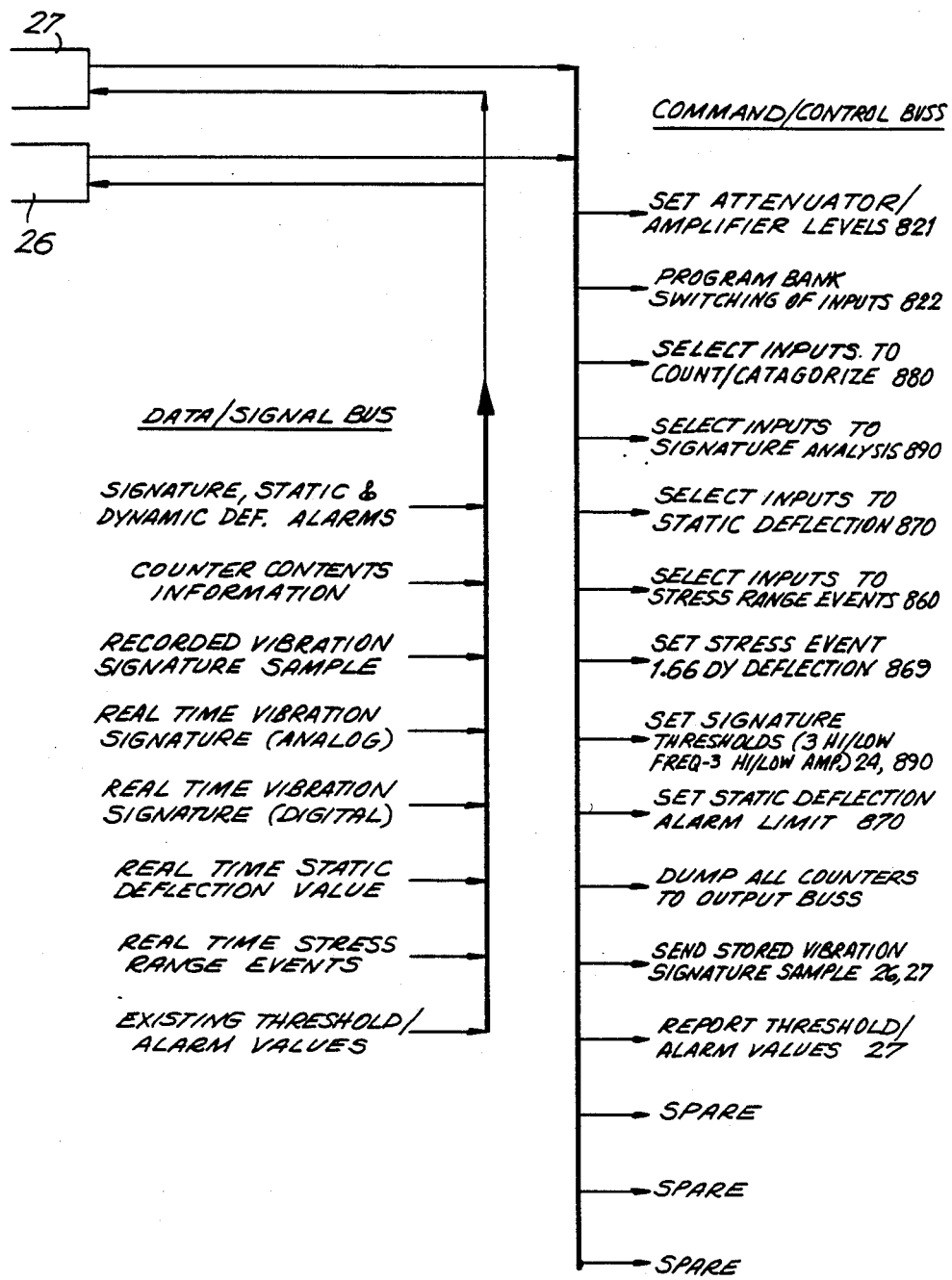
FIG. 13 is a flow chart for a remote electronics unit for detected sounds acquisition and analysis in accordance with the present invention.

Referring to FIGS. 1, 8, and 13, electronics unit 20 receives and processes the sound signals detected by sensor 10 and develops data for the analyses of the present invention as described herein. Electronics unit 20 is preferably configured to be a self-contained unit that can be located proximate to the structural member being monitored and includes power supply 25, signal conditioning unit 21, control module 24, switching-multiplex unit 22, and signal processing unit 23.

Power supply 25 may be any conventional power supply capable of providing the desired voltages for operating the data acquisition and signal processing operations of sensor 10 and electronics unit 20. Control module 24 may be any conventional microprocessor based device capable of manipulating the acquired data signals from sensor 10 and to control the processing of the signals through signal conditioning unit 21, switching-multiplex unit 22 and signal processing unit 23 as described herein. Switching-multiplex unit 22 may be any appropriate device for switching and/or multiplexing the signals to any one or more of the desired analysis modules or memory or transmission port as desired, and has associated with it a data bus (not shown) for passing the detected signals among the various components of electronics unit 20.

Signal conditioning unit 21 is configured to receive the signals from sensor 10 and to provide the detected signals with a desired amplitude that is within the range of subsequent signal processing devices using, for example, attenuators, preamplifiers, and amplifiers. Preferably, electronics unit 20 includes an analog to digital convertor device for converting the detected signals into digital data for processing by signal processing unit 23 or transmission via port 27 to a remotely located signal processing device, at, for example, central station 30, or both. In embodiments where sensor 10 obtains a plurality of signals, electronics unit 20 may have a multichannel input and signal conditioning section for separately processing each detected signal. The multiplexor 22 may be adapted for selectively processing one detected signal at a time, or for a combination of multichannel and single channel processing.

Signal processing unit 23 thus obtains the detected conditioned sound data in a processable form, and performs the operations for obtaining the desired measurements and indicating the appropriate alarms which are described in greater detail below.

The output of the analysis units of electronics unit 20 may be displayed on a conventional display device (not shown) appropriate for the parameter or parameters being measured, for example, a CRT monitor, an oscilloscope, a paper tracing recorder, a frequency spectrum plot, or numerical displays for data such as the count, the mass or speed of a transient load. Electronics unit 20 may include onsite port 26 for providing local access to the information by, for example, a portable display device or a portable signal processing unit that can be plugged into electronics unit 20 and used to obtain the detected signals, in analog or digital form, the measurements made and/or alarms generated by an analysis unit of electronics units as desired by, for example, a person inspecting the structural member being monitored.

Similarly, the signals being processed by electronics unit 20, before or after processing by processing unit 23, may be communicated over communications network 60 connected to telemetry port 27 of electronics unit 20 and telemetry port 37 of central station 30 to central monitoring station 30 for evaluation. Any conventional data communications network, including microwave, telephone line, satellite, or recorded magnetic medium, appropriate for transferring any of these signals in any or each of real time, time delay, time share or batch formats may be used.

In one preferred embodiment, the present invention is adapted for monitoring a structural member that is a support beam for a bridge or bridge span. Such spans are typically made from steel girders covered by a roadbed of reinforced concrete and having a length of about 20 to 120 feet and from about 30 feet to about 60 feet across. In the longitudinal dimension, the natural frequency of such girders ranges from about 65 to about 400 Hz. The expected number of harmonics would include, for example, the 900th order harmonic, although in many instances harmonics below the 900th harmonics will be sufficient. In the vertical dimension, the natural fundamental frequency is below 10 Hz. Each structure typically will have a unique fundamental frequency in each dimension in accordance with its actual construction, composition, and configuration.

The structural acoustic signature for such structures may include sonic and infrasonic frequencies, for example, from about 0.1 Hz to about 20 kHz, although greater or lesser ranges could be used based upon the actual dimensions and the possible number of harmonics that could be supported by the member given its inherent damping, elasticity, and the magnitude of the transient loading.

Simple girders bridge spans typically have an expansion joint on either end which acoustically isolates the support beams. In this regard, the speed of sound or acoustical wave frequencies passing through a steel I-beam is about 15,030 feet per second, whereas the corresponding speed through air is about 1,000 feet per second. Consequently, the air gap between adjacent beams interposes a significant impedance and substantially reduces sound transmission corresponding to the motion of a beam to its adjacent beams, thereby providing sufficient acoustical isolation.

If, instead, the I-beams were rigidly bolted or welded together, they would comprise a single complex acoustical transmission line segment as the vibrations would travel across the rigid joint substantially unattenuated. In this instance, the standing wave frequency would depend upon the length of the complex structural member in that dimension. Complex structural configurations or assemblages may have more than two supports supporting the composite structural member and more than one point of maximum deflection.

Referring to FIGS. 2a through 2h, a series of illustrative waveforms are shown of the output of accelerometer sensors, secured to a structural member, in response to transient loads of four different masses—light, medium, heavy, and very heavy—being applied at two rates—slow and fast. As the load gets heavier, or is applied faster, both the relative magnitude and the shape of the waveform will change as may be seen from the illustrations. When heavy and very heavy loads are applied, the structural member will continue to oscillate for a short period of time even when it is highly damped, as would be the case for a girder beam of a highway bridge with a concrete roadway surface. For very heavy loads, three or more of these oscillations may be detected.

Figure 2I:
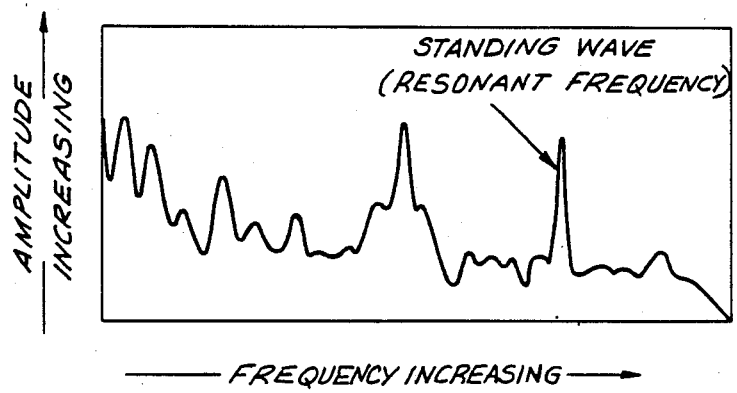
FIGS. 2(i) and 2(j) are respectively illustrative plots of a waveform generated by a structural member in response to and subsequent to a transient load in the frequency domain before and after the occurrence of a defect.
Figure 2J:
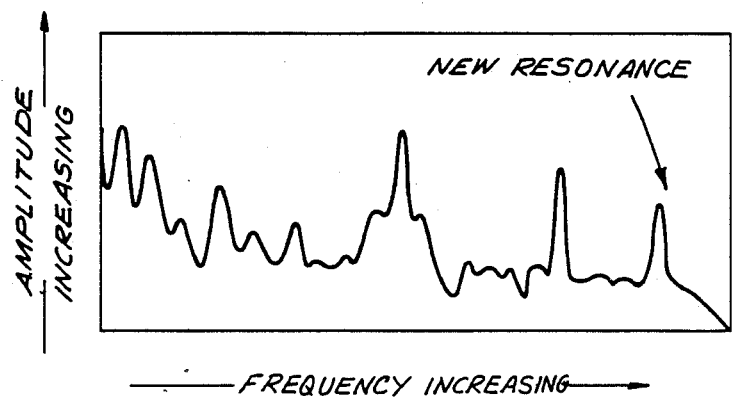

Referring to FIGS. 2i and 2j, illustrations are shown of representative structural acoustic signatures that are the outputs of a fast Fourier transform processor from signals input from an accelerometer sensor mounted on a structural member. A standing wave or resonance of the structural member is shown as labeled in FIG. 2i when the structure is first monitored. This standing wave frequency and amplitude would be one component of the baseline structural acoustic signature of the structural member taken along a first dimension.

FIG. 2j illustrates a structural acoustic signature obtained at a subsequent time from the same sensor and structural member of the signal shown in FIG. 2i. In this signature, a new standing wave or resonance at a higher frequency exists and the amplitude of the original standing wave or resonance is somewhat reduced. The change in these components of the structural acoustic signature from the baseline structural acoustic signature indicate a measured change in the structural integrity of the structural member, possibly from a defect such as a crack in the girder, and would indicate that further analysis and possibly an onsite inspection of the structural member should be conducted.

Figure 3:
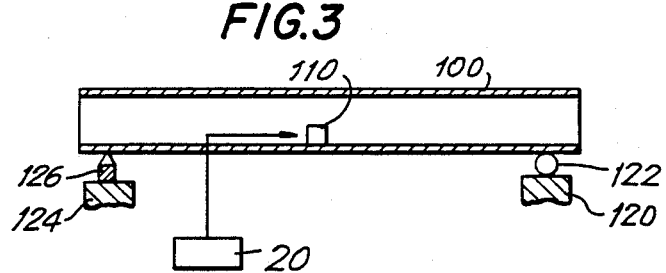
FIG. 3 is a schematic representation of a monitoring configuration of an embodiment of the invention.

Referring to FIG. 3, in one embodiment of the invention, sensor 110 is an accelerometer permanently secured to member 100 and oriented to detect acceleration in the vertical dimension of member 100. Member 100 is illustrated to be, for example, a steel I-beam that is supported at one end by pier 120 and roller 122, and at the other end by pier 124 and anchor 126, having a natural frequency in the longitudinal dimension that is inversely proportional to its longitudinal length.

Although sensor 110 may be placed anywhere along the surface of member 100 to detect the desired frequencies, sensor 110 is preferably placed where the vibrations of structural member 100 along the dimension of interest likely will be the greatest, for example, at the maximum displacement of member 100. However, in circumstances where the transient load impacts the structural member at more than one point along the member, as may occur in the vehicle/bridge environment, a more preferred location for sensor 110 would be proximate to the location of greatest impact. For example, an expansion joint seperating adjacent bridge spans may be elevated above or depressed below the road surface and thus serve to provide the vehicle with additional oscillations that would increase the effect of its impact and cause the location of maximum vibration to be closer to the expansion joint where the vehicle firsts contacts the span, rather than in the middle of the span.

Referring to FIG. 4, another embodiment of the invention illustrates an alternate sensor configuration whereby sensor 10 includes triaxial accelerometer sensor 112 and seismic accelerometer 114. Triaxial accelerometer 112 may be located anywhere on member 100, preferably at about the location where the impact force is likely to be the greatest, e.g., at one end of member 100.

Seismic accelerometer 114 is sensitive to low frequency vibrations, typically frequencies less than about 500 Hz, and is particularly useful for measuring the vertical displacement of member 100 as it is subjected to a transient load. Accordingly, for this purpose, seismic accelerometer 114 is preferably placed at a point where the greatest deflection of member 100 in response to the transient load is expected to occur.

Triaxial accelerometers are selected to have characteristics that are better suited to monitor and detect changes in the higher harmonics of the waveform signature of a structural member. Seismic accelerometers are selected to have characteristics that are better suited to monitor and detect changes in deflection and the lower frequencies and fundamental frequencies of the waveform signature of a structural member.

Figure 5:
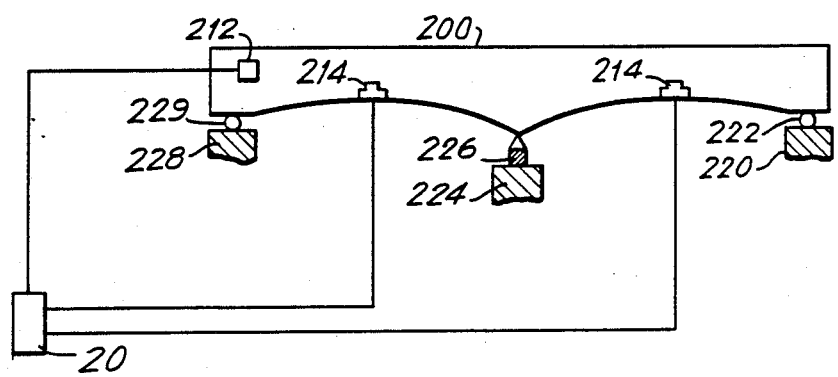
FIG. 5 is a schematic representation of a bridge support member and the transducer locations for monitoring such member in accordance with an embodiment of the present invention.

Referring now to FIG. 5, an alternate embodiment of the sensor apparatus of the present invention is shown. Structural member 200 is illustrated to be a beam supported at three points by piers 220, 224, and 228, fixedly anchored to pier 224 at about its midpoint by anchor pin 226, and movably connected to piers 220 and 228 by rollers 222 and 229, respectively, at about the endpoints of member 200. Thus, member 200 comprises a single structural member, notwithstanding that it has two locations of likely maximum deflections, one between piers 220 and 224 and one between piers 224 and 228. Such structural members include continuous span bridges which may be, for example, a single bolted, riveted, or welded structure or any plurality of elements rigidly interconnected.

In this embodiment, seismic accelerometers 214 are secured to member 200 proximate to the two points of maximum deflection, oriented to measure vertical movement of member 200 as it is subjected to a transient load. Triaxial accelerometer 212 is secured on member 200 at a location proximate to an end of member 200 to obtain the benefit of sensing the maximum impact of a transient load on member 200 crossing the expansion joint from the adjoining span or roadway. The individual accelerometers of triaxial accelerometer 212 are orthogonally oriented in alignment with the longitudinal, vertical, and transverse dimensions of member 200.

Referring to FIG. 6, one implementation of the apparatus of the invention is shown. In this embodiment, bridge 650 comprises a plurality of structural support girder beams 600 arranged three beams across. The bridge consists of two spans with bridge deck 660 resting on plurality of beams 600. Beams 600 are separated by expansion joints (not shown), and are supported by a plurality o piers at the ends of the beams and under the expansion joints (not shown). Plurality of sensors 612 are secured to the plurality of beams at about the point of maximum deflection of the beam to measure separately the sounds transmitted by each beam respectively. Preferably, sensors 612 are accelerometer devices, more preferably seismic accelerometers. The outputs of accelerometers 612, which may a single channel or, in the case of a triaxial accelerometers, three channels, are passed to electronics unit 20 (described elsewhere herein) by conventional coaxial or ribbon cables 655.

Figure 7:
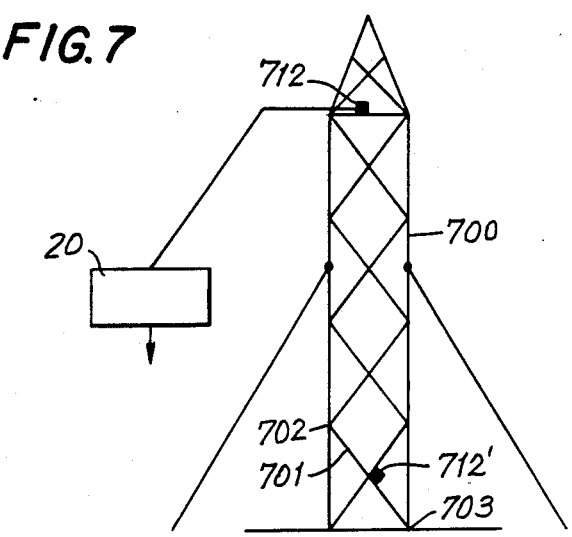
FIG. 7 is a schematic representation of an alternative embodiment transducer location for monitoring an antenna tower in accordance with an alternate embodiment of the present invention.

Referring to FIGS. 1 and 7, the apparatus of the present invention is shown in the context of a radio tower structural member. Structural member 700 is a radio tower comprised of a plurality of separate elements rigidly interconnected. The complete structure is capable of supporting a standing wave as an entity as there is a gross motion of the tower in response to various transient loads, for example, gusts of wind, that can be detected.

Alternately, various structural components of tower 700 may be capable of supporting a standing wave at different frequencies than the complete tower. For example, girder 701 may be rigidly fixed between two points 702 and 703 as part of tower 700 and capable of transmitting sounds distinguishable from the sounds transmitted by its adjacent structural members and the tower as a whole. In this regard, the magnitude of the frequencies sensed on girder 701 are expected to be greater than, and distinguishable from the frequencies corresponding to the tower as a whole and from adjacent girders sensed on girder 701. Conversely, by evaluating the lower frequencies and amplitudes, the waveform signatures of tower 700 as a structure can be obtained and monitored.

In the embodiment depicted in FIG. 7, accelerometer 712 is secured to tower 700 and accelerometer 712' is secured to girder 701 at points of, and oriented to detect, maximum deflection of each. Preferably, accelerometer 712 is a seismic accelerometer capable of detecting the lower frequencies to measure further the displacement or sway of the tower.

Referring to FIGS. 1, 8, and 13, a central station monitoring system in accordance with a preferred embodiment of the present invention is shown. In this embodiment, central station 30 receives data via communications network 60 from a plurality remote electronics unit 820 (only one unit 820 is shown). Electronics unit 820 is secured proximate to the structural member or members to be monitored and electrically connected to sensor 10. Sensor 10 is secured to the structural member or members to be monitored at that remote station, and may include a plurality of sensors for detecting sound transmitted by the structural member or by more than one structural member along one or more dimensions.

Remote electronics unit 820 includes control module 24 for controlling the various signal acquisition, transfer, and processing functions of unit 820, analysis module 860 for determining and counting stress range events, analysis module 870 for determining the maximum detected deflection, analysis module 880 for categorizing the transient loads, and analysis module 890 for detected changes in structural integrity of the structural member being monitored.

Control module 24 is preferably a microprocessor device that is programmed to control electronics unit 820 to perform automatically its various functions in accordance with a predetermined protocol and, optionally, to perform various functions under remote control in accordance with instructions provided by an external control module, for example, signal processor 46 of central monitoring station 30 connected via communications network 60 through telemetry ports 27 and 37, or a similar device in a portable monitoring station connected through local port 26 that might be used by a person investigating the structural member. Such an external processor may be used to override or to be used concurrently with remote control module 24 to monitor the structural member through its own analysis units or using the analysis modules of electronics unit 820 or both.

Remote control operation of electronics unit 820 might include, for example, injecting diagnostic test signals and/or adjusting the instrumentation or processing parameters for electronics unit 820 or sensor 10, to obtain real time signals from electronics unit 820 for analysis or processing, or to obtain stored information from the various analysis modules of electronics unit 820.

In this embodiment, electronics unit 820 and sensor 10 are configured to monitor a highway bridge span having three lanes of traffic having of nine simple girders as main support members (not shown). It is believed sufficient that sensor 10 includes discrete transducers placed and secured on the three girders under or near the center of each of the three traffic lanes (not shown), although discrete transducers could be placed on all nine girders, if desired. Sensor 10 is configured to include a plurality of discrete transducers each of which includes an arrangement of entry accelerometer 804, seismic accelerometer 806, and exit accelerometer 808 for each structural member or girder (discrete transducers for only one girder are shown in FIG. 8). Entry and exit accelerometers 804 and 808 are located near the ends of the girder and oriented to detect sound in the vertical dimension. Seismic accelerometer 806 is located in the center of the girder at the point of maximum deflection and oriented to detect displacement of the girder in the vertical dimension.

Sensor 10 also may include as a part of each discrete transducer arrangement clinometer sensor 802 to detect a static deflection condition, i.e., a condition when the structure either has been subjected to a gradual increase in loading that can not be detected by the dynamic measurements, e.g., by traffic moving too slowly to stimulate the accelerometers to obtain accurate measurements, or to detect a change in the tilt, i.e., a change from a vertical or neutral orientation in an unloaded condition. Such a clinometer sensor may be a CG-505 tilt sensor device, manufactured by Spectron Glass and Electronics, Inc., of Hauppauge N.Y., and is located on the structural member at a point where static load conditions will cause angular movement of the structural member that can be detected, and preferably at or near a girder support point, e.g., over a rocker or pin type bearing.

Clinometer 802 is adapted to measure angular changes of the member and to provide a signal whenever the structural member changes from its neutral position, thus indicating an active deflection condition exists. However, logic circuit gate 876 is provided so that a deflection condition signal from clinometer 802 will be ignored unless the signals from accelerometers indicate that the structure is essentially at rest. Thus, clinometer 802 will not initiate an alarm condition unless the structure is determined to be essentially at rest dynamically and is in a position which indicates a potentially dangerous deflection condition.

Each discrete signal obtained by the transducers of sensor 10 is passed to electronics unit 20 which, in this embodiment, is configured to have a multichannel signal conditioning unit 821 and switching/multiplex device 822 to amplify and/or attenuate each actual detected signal separately, to be in a desired voltage range for subsequent analog to digital conversion or analog signal processing. A typical output voltage range may include from about 0 to about ±10 volts. Signal conditioning unit 821 may be controllable by control module 24 to adjust the circuit parameters to obtain the desired output signal levels for each detected signal.

The conditioned signals output from unit 821 are then passed to switching/multiplex unit 822 preferably a microprocessor controlled device, e.g., Analog Devices No. 7501, manufactured by Analog Devices, of Norwood, Mass., which performs the switching and multiplexing of signals and provides the clock and timer pulses for controlling the sampling of data to the appropriate analysis units from the selected girders.

Referring to FIGS. 1, 8, and 11, analysis module 880 evaluates the data from entry accelerometer 804 and exit accelerometer 808 of a discrete transducer arrangement and performs a count of the number of vehicles that have crossed the structural member being monitored, i.e., the monitored girder. The detected signals are separately adjusted by unit 821 to be within ±10 volts DC and passed through analog circuit 881 to differentiate changes in the detected waveform and correlate the entry and exit of each vehicle to count the number of vehicles. Digitization of the analog signal may occur at a sampling rate of approximately 25 kHz, more preferably 10 kHz. This rate may be the same for all of the modules of electronics unit 820.

Circuit 881 further includes circuits for differentiating the relative magnitude of each vehicle based on the duration and shape of the waveform amplitude of the detected analog signals in order to classify the magnitude of the load. Preferably, a zener diode bridge is used to generate a voltage signal corresponding to the magnitude of the detected signals so that the voltage of the zener diodes corresponds to the different categories. For convenience, the magnitudes are typically divided into four classes, light loads, medium loads, heavy load, and very heavy loads, the first class corresponding to automobiles and latter class corresponding to vehicles that are overweight for the rated load capability of the roadway or bridge span.

Once the magnitude of the load has been determined, counter 882 having a register for each class of load, is actuated so that the appropriate register is advanced one count. Counter 882 will continue to accumulate the number of detected transient loads by determined class of weight until the stored information is requested by control module 24, whereupon counter 882 resets.

Information and data from module 880 may be made available, via control module 24, to onsite port 26 or to telemetry port 27 for data analysis at the bridge location or at central monitoring station 30, respectively.

Referring to FIGS. 1, 8 and 12, signature analysis module 890 processes the detected sound signals and provides an alarm condition signal if the structual acoustic signature for the structural member is determined to change significantly. Detected frequency information from one of the accelerometers in a discrete transducer unit of sensor 10 is selected by control module 24 and transmitted to signature analysis module 890. Control module 24 may be operating under software control or in an interrupt mode in response to instructions provided by central monitoring station 30 or other external processing unit.

The selected detected signals are passed to analog to digital converter 892, and then passed to transform circuit 894 for transforming the detected broadband signals into discrete frequency signals having amplitudes and frequencies defining the structural acoustic signature. Transform circuit 1394 is preferably a fast Fourier transform device. The discrete frequency domain signals are then passed to circuit 896 for analyzing the amplitudes and frequencies of the determined signature, and comparing the amplitudes and frequencies to the selected signature thresholds. Circuits 894 and 896 are functionally similar to a Model 5840A Analyzer manufactured by Rockland Scientific Corp. of Rockleigh, N.J.

The threshold values are selected by control module 24 to define windows to correspond to the limits of the normal or baseline structural acoustic signature of the structural member as monitored by the particular accelerometer sensor providing the signals being analyzed. The threshold values may be adjusted to account for changes in the ambient environment or weather. Thus, when detected components of the structural acoustic signature cross the threshold signals, or occur outside the windows of normal operation established by the threshold signals, an alarm is generated.

The device may be configured to provide up to three windows, more preferably one or two windows corresponding to significant resonant frequencies. The amplitude threshold window may include a range of about ±10% to about ±25 of the normal or baseline amplitude and the frequency threshold window may include a range of about ±2% to about ±10%, more preferably ±2% to about ±5% of the normal or baseline frequency. More than three windows could be used with the addition of appropriate circuits for providing such windows and comparing the detected signature to the windows.

In one embodiment, the degree of an "out of window" alarm condition may be measured and compared to a separate threshold value so that determined large changes can be identified. Thus, the occurrence of a large change could be used, for example, to actuate a gate across a roadway to close the road to traffic until the structural member can be inspected.

In the preferred embodiment, the structural acoustic signatures includes the portion of the detected signals corresponding to the continued vibration of the span after a vehicle has excited and passed over the bridge span being monitored and before the next vehicle enters the span. Accordingly, the other analysis modules of electronics unit 820 may be used to confirm that no vehicles are on the span so that the signature analysis can be performed. For example, a control signal "NO TRAFFIC" may be provided by analysis unit 880 to indicate that no traffic is on the span and that it is an acceptable time to process the detected acoustic information to obtain a signal signature for analysis.

Analysis unit 890 also may be configured with port 891 for providing real time signals of the detected sounds in analog form and/or with port 893 for providing the detected signals in digital form. Module 890 also may include memory device 897 for recording a predetermined amount of digitized signals for subsequent processing, e.g., six minutes of signals to be accessed by central monitoring station 30 via telemetry port 27 or locally via port 26 for analysis to confirm alarm conditions, or to evaluate the instrumentation or threshold parameters and the like. Ports 891 and 893 may be connected to one or both of local port 26 or telemetry port 27.

Figure 9:
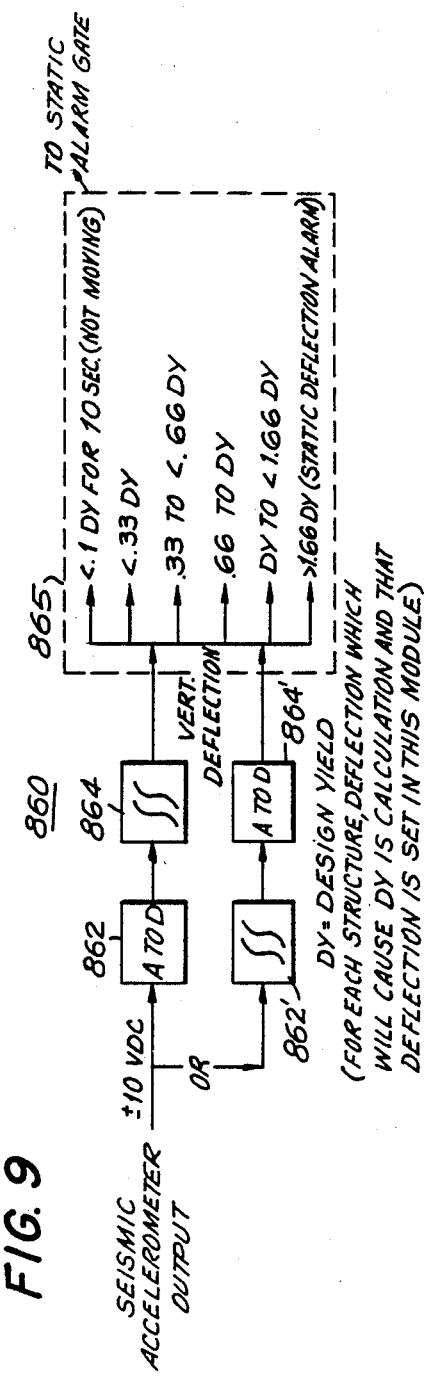
FIG. 9 is a block diagram for determining Stress Range Events of a structural member subjected to transient loads in accordance with the present invention.

Referring to FIGS. 1, 8, and 9, analysis module 860 analyzes the fundamental mode of structural vibration in the vertical axis to determine stress range events. It is provided to obtain information regarding the deflection of the structural member due to transient loads impacting the structural member being monitored. The signal detected by seismic acclerometer 806 is obtained, digitized by analog to digital converter 862, and passed through double integration circuit 864 to provide a signal corresponding to the deflection of the structure in the vertical direction. Alternately, the signal could be double integrated first by circuit 862' and then digitized by circuit 864'. The resulting signal is proportional to the displacement or deflection of the monitored structural member at the location of seismometer sensor 806 (or other seismometer sensor appropriately located). The deflection signal is numerically compared with preset values in order to count the number of events and to characterize each event based upon the severity, i.e., the size of each peak-to-peak deflection value.

In the case of a bridge girder, for example, the downward deflection from the neutral position might be represented by a positive voltage peak while deflections above the neutral position would be represented by a negative voltage peak. A stress range event is herein defined as either (1) movement from a maximum downward position to a maximum upward position, or (2) movement from a maximum upward position to a maximum downward position.

Calculations for any deflection from neutral can provide the amount of yield stress imposed on the girder in the vicinity of the sensor. By adding the absolute value of the negative voltage peak to the absolute value of the subsequent positive voltage peak (or the absolute value of the positive voltage peak to the absolute value of the subsequent negative voltage peak) one can obtain a value which is proportional to the stress range of the event represented by one half cycle of the vibration of the girder in the vertical direction (dimension) of measurement. The magnitude of each peak-to-peak sum is then compared to a reference value to categorize the event into one of several categories or ranges, each range being a specified percentage of the design yield of the material of the girder. After categorization, the event is stored as one count in appropriate storage register 868 having subregisters or counters for each category. Preferably, all stress range events whose peak-to-peak value equals or exceeds a value representative of ten percent (10%) of the design yield are counted and stored for later retrieval.

Stress range events module 860 also is provided with alarm circuit 869 for comparing the detected value with a predetermined threshold signal value corresponding to the maximum allowable deflection of the structural member so that when the threshold is exceeded, a "DYNAMIC DEFLECTION" alarm signal is generated.

Stress range events module 860 also generates a "BRIDGE MOVING" control signal corresponding to when the structural member is moving in the vertical dimension, which signal is used by gate 876 associated with module 870 to block the generation of a static alarm condition resulting from dynamic movement of the bridge.

Stress range events module 860 also may have an output port 867 that can be accessed by local port 26 for providing a real time signal for data analysis at the remote location and/or telemetry port 27 for analysis at central station 30.

Stress range event module 860 thus provides a dynamic history and generates alarm signals of selected deflection events. Categorization of transient load events indicate the number and degree of fatigue inducing events that the structural member has undergone during the period in which information is stored in storage registers 865 to be accessed by control module 24. When information is accessed, register 868 is cleared and new data is accumulated. Alarm signals are generated whenever a transient load event exceeds a specified threshold value, which indicates that the maximum desired deflection has been exceeded during a dynamic event. The alarm signal may be used further to activate other onsite activities such as an indicating the existance of an excessive loading or causing a photograph to be taken of a potentially over-weight vehicle, or causing a detectable marking to be applied to the designated over-weight vehicle so that proper authorities can investigate the vehicle and assess any appropriate fines or taxes.

Figure 10:
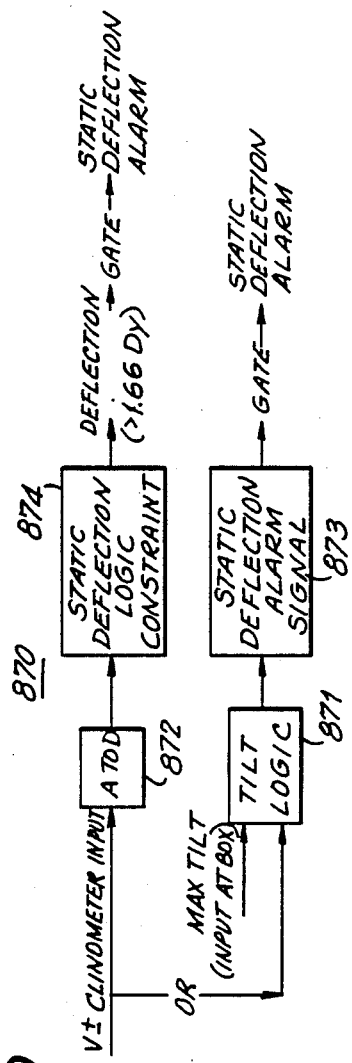
FIG. 10 is a block diagram for determining the static tilt of a structural member in accordance with the present invention.

Refering to FIGS. 1, 8, and 10, analysis module 870 is a Tilt Detection module which provides an indication of the tilt of the structural member being monitored from a normal neutral position corresponding to no dynamic stress and no transient loads. In the preferred embodiment, tilt is indicated by measuring the angular change of the structural member at the clinometer transducer location. The signals from clinometer 1802 are passed to analog to digital converter 1872, and then to static deflection logic circuit 1374 whereby changes in clinometer orientation provide signals containing angular orientation data. If the clinometer signals correspond to angles greater than preselected angles, an alarm condition is declared to exist. Generation of an alarm signal is blocked, however, so long as module 860 provides the BRIDGE MOVING signal to close logic gate 876. Thus, alarms will be generated only when the structural member is determined to be essentially at rest and at an abnormal angle relative to a normal neutral position. In one embodiment, an alarm signal is generated if the detected deflection equates to a stress that exceeds about 1.66 times the design yield.

In an alternative implementation, the signal from clinometer 802 could be passed to comparator 871 where it is compared to a threshold signal corresponding to the maximum allowable tilt of the structural member. Thus, an alarm condition is declared by logic circuit 873 if the threshold is exceeded, and an alarm signal generated if gate 876 is open.

Analysis module 870 also may provide for access to a real time signal for data analysis at the remote location via, for example, local port 26 or at central station 30 via, for example, telemetry port 27.

In an alternate embodiment, analysis module 870 may be constructed to determine the maximum detected deflection of the structural member during a selected time period and, for each period, store the maximum value. During the selected time period, e.g., five minutes of real time, any signal detected that is greater than the stored signal replaces the stored signal in a temporary storage register. At the end of the predetermined period, the value in the temporary storage register is stored in a separate storage register. The peak value for each successive period is obtained and stored. The contents of the storage register are dumped when the accumulated deflection data is requested by control module 24, typically upon instructions from central monitoring station 30.

In one embodiment, communication between remote electronics unit 820 and central monitoring station 30 occurs when an alarm signal is generated by an analysis module of remote electronic unit 820 so that the alarm can be transferred to central monitoring station 30, when central monitoring station 30 polls remote electronics unit 820 to obtain accumulated data, or when central monitoring station 30 is initializing or adjusting the parameters of remote electronics unit 820, conducting equipment tests, or conducting real time analysis of the structural member or transient loads. By limiting communications in this manner and limiting the quantum of data accumulated by each remote station, a large number of remote units, ranging from one to tens of thousands, can be connected to a single central monitoring station.

Central monitoring station 30 is preferably adapted to evaluate separately the data obtained by each remote electronics unit 820. It receives any alarms and the stored historical data, and may provide for the operator to perform adjustments to the remote electronics unit and/or real time evaluation of any structural member as the need arises. Thus, when anomalies or alarms occur, the operator may evaluate the specific remote structural member in or close to real time, for example, to confirm or reject an alarm condition, to review historical data for that structural member, or to make appropriate corrections or changes to the instrumentation configuration or threshold settings for alarm signals. Central station 30 may be provided with local access port 36 to obtain or to display signals as they are being processed by station 30 or to obtain stored data for further analysis by external equipment.

In the preferred embodiment, central monitoring station 30 automatically periodically polls each remote electronics unit 820 and retrieves data stored by the remote unit. The historical data can then be compared to historical data previously obtained from that unit, e.g., of the prior day, week, month, or year, and can generate an appropriate alert condition if any of the recently detected parameters vary significantly from prior historical data. The generation of alerts in this instance indicate that further investigation of the structural member may be warranted.

A significant variation of the total number of transient loads indicates greater use which can be related to useful life of the structural element. For structures such as highway bridges, the count relates generally to the number of vehicles and greater use can be attributed to increased traffic flow. A significant variation of the magnitude of the transient loading can be related to the type of use.

For structures such as highway bridges, the magnitude of the transient loading and the detected stress events can be evaluated with the number of loads so that, if the number of heavier loads increase without a corresponding increase in the number of vehicles, then the change may be related to a discontinuity, e.g., a pothole or bump, in the roadway prior to the span itself that is increasing the impact of each vehicle on the span. Alternately, it could represent an increase in heavy truck traffic, for example, caused by construction elsewhere.

A significant change in the maximum detected deflection over time indicates a change in some structural characteristic, e.g., elasticity. However, if the change is accompanied by an increase in the number of transient loads, then it may merely reflect large amounts of transient loads. In the bridge context, this may reflect large amounts of traffic on the span, which may be a result of congestion. Similarly, if increased deflection corresponded to an increased number of heavy transient loads, then the signal changes may be due to a discontinuity in the pavement, e.g., a pothole.

Once the cause of an alarm signal has been diagnosed, a visual inspection of the structure can be scheduled to occur in accordance with the determined severity of the identified change. In many circumstances, a brief visual inspection can either confirm the diagnosis or confirm that a more thorough investigation is required. This permits allocating resources more efficiently so that inspections and any appropriate repairs can be performed in an orderly manner.

Another advantage of this embodiment is that the central processing station can collect data over long time periods and plot historical trends to project future needs regarding the use and maintenance of the various structural members being monitored.

Referring to FIGS. 1 and 13, the present invention also provides for a method of measuring changes in the structural integrity of a structural member. In one embodiment, that method includes:

(a) detecting the sound present in the structural member along a given dimension in response to a transient load within the sonic and infrasonic frequency range including the natural fundamental and harmonic frequencies of the structural member;

(b) subjecting the structural member to a first transient load having a first mass;

(c) determining a first structural acoustic signature from the detected sounds transmitted through the structural member along the given dimension in response to the first transient load, said first structural acoustic signature including the fundamental and harmonic frequencies transmitted subsequent to the first transient load;

(d) subjecting the structural member to a second transient load having a second mass;

(e) determining a second structural acoustic signature from the detected sounds transmitted by the structural member along the given dimension in response to the the second transient load, said second structural acoustic signature including the fundamental and harmonic frequencies transmitted subsequent to the second transient load;

(f) comparing the second structural acoustic signature to the first structural acoustic signature; and (g) determining that there has been a change in structural characteristics when the fundamental or harmonic frequencies of the second structural acoustics signature differ from the fundamental or harmonic frequencies of the first structural acoustic signature by more than a predetermined amount.

In one embodiment of the foregoing method, step (a) is conducted at the remote electrical unit 820 for each structural member and further includes converting the analog signals into digital signals and storing the structural acoustic signature samples in a temporary storage device for subsequent transmission to the central monitoring station, and steps (c), (e), (f), and (g) are conducted at a central monitoring station.

In a preferred embodiment, the first and second transient loads are of substantially the same mass and duration, and the predetermined amount is selected to provide a tolerance for changes in elasticity of the structural member as a result different weather or environmental conditions.

In one preferred embodiment, detecting the sound frequencies present in the structural member further comprises detecting the motion of the structural member along one selected dimension, more preferably along two selected dimensions, in response to the transient load using, for example, accelerometer devices. The structural acoustic signature will include sound frequencies naturally present in the structural member in one dimension of the structural member. For example, in connection with a bridge span support beam, frequencies present along the longtudinal dimension and in the vertical dimension may be separately detected and compared to previously obtained reference frequencies in the structural acoustic signatures to determine whether there are differences in the fundamental or harmonic frequencies corresponding to changes in structural integrity, more specifically, elasticity or stiffness. In other embodiments, a third dimension also could be detected, such as the lateral motion transverse to the longitudinal axis of the beam. Preferably, the signals in the different dimensions are separately obtained and compared, although it is possible to obtain and compare composite signals including all the dimensions detected.

Importantly, it has been discovered that, in many instances, changes in the frequencies that make up the structural acoustic signature are more easily detected and identifiable at the higher harmonic frequencies, i.e., harmonics at or greater than about the 200th harmonic, thus providing for more accurate or enhanced identification of changes in structural integrity. For example, a structural member that is a conventional 90-foot long steel I-beam supported at its ends having a normal elasticity will have a fundamental frequency at about 1.5 Hz. When the elasticity changes with use, the fundamental frequency may change slightly only to 1.6 Hz. Such a change, although detectable, is not a large change and may not be immediately recognized. However, the corresponding change at higher order harmonics is greater and, thus, easier to detect. For example, at the 200th harmonic frequency, 300 Hz, the change is expected to be about 20 Hz, which is easier to detect than a 0.1 Hz change at the fundamental frequency. Thus, detection of a change at a higher harmonic frequency may be used, for example, to evaluate more thoroughly the lower frequencies to determine whether a large number of fundamental or harmonic frequencies have shifted, corresponding to a defect, or whether the detected change was an abnormality.

In another preferred embodiment, the components of the structural acoustic signature also are obtained at different locations on the structural members. This embodiment permits obtaining two measurements of the response of the member to the same transient load and permits making two independent determinations of whether there has been a change in the signature corresponding to a change in the structural integrity or elasticity (stiffness) of the member. Moreover, the independent determinations can be correlated, and the correlation can be used to enhance the confidence factor of the determination made. In particular, the concurrence of detected shifts in fundamental or harmonic frequencies, or the concurrence of newly detected fundamental or harmonic frequencies by one or more sensors would confirm the reliability of the independently made determinations.

Further, multiple transducers at multiple locations on the same structural member, including even different types of transducers for detecting the sounds transmitted by the structural member in response to a transient load, may be used.

The detection of new resonant frequencies or standing wave frequencies associated with a localized defect in the structural member also can be used to determine the relative location of the defect by correlating the measure of the pertinent dimension of the member along which the sound is being detected to the determined fundamental wavelength attributed to the defect location, and thereby determining a distance from one end of the structural member where the defect would be expected to be located. By detecting the resonant frequency along more than one dimension, and correlating the new resonant frequencies attributed to the defect in the multiple dimensions, the location of the defect in the structural member can be more precisely determined.

In one embodiment of the invention, the first transient load and first structural acoustic signature may be used as a reference or baseline signature of the structural element so that each subsequently acquired signature sample in response to a transient load is compared to the first reference signature. In this embodiment, if the structural member can be properly certified as safe for its intended purpose immediately after the first transient load, then the baseline signature can be used to detect absolute changes to structural integrity regarding optimal safety, in addition to relative changes. In an alternate embodiment, a dynamic comparison of a subsequent signature sample to the preceding signature sample may be made whereby each after acquired signature sample is compared to the immediately (or a recently obtained) preceding signature sample.

In the former embodiment, adjustments or tolerance limits for differences in environmental conditions may be required as explained herein, whereas in the latter embodiment, such adjustments may be smaller or minimized, particularly if the time between transient loads is not so great that there can be a substantial environmental change. Further, a combination of both embodiments may be used so that the response to the most recent transient load can be compared to a response to a relatively recent prior transient load under similar environmental conditions. A fixed baseline reference signature could be used to identify any gradual shift in the fundamental and harmonic frequencies as a result of defects occurring gradually that might be ignored if only recent data were compared. In this manner, measurements taken on, for example a bridge span support beam from one day to the next at the same relative time of the day will provide a sliding point of reference for evaluating the sound transmission of the member in response to a transient load under similar environmental conditions as those conditions gradually change. Thus, if a substantial change is detected, it can be readily ascertained whether it is likely to be a false alarm as a result of a dramatic environmental change or a real alarm as a result of a crack, fracture, or other problem that requires further investigation.

The predetermined amount by which the fundamental or harmonic frequencies of the second structural acoustic signature sample may differ from the fundamental or harmonic frequencies of the first structural acoustic signature without generating an alarm is to correspond to changes in elasticity of the structural member because of changes in the ambient weather or environmental conditions. This amount may be determined by subjecting the structural member in question to a sample transient load of a known and substantially identical mass under different environmental weather conditions and determining the range of relative changes in the signature caused by the environmental changes, confirming that there has been no change in the structural integrity of the structural member, and thereby compensating the first structural acoustic signature for the detected range of environmental changes. The above method of the present invention could then further include monitoring the environmental condition when the first and second transient loads impact the structural member, and adjusting the predetermined amount to correspond to the difference in detected environmental conditions based on the predetermined relationship of change in elasticity to change in environment.

In yet another embodiment, the determinied response of the structural member to a transient load may be compared to a plurality of signals corresponding to one or more categories of transient loads. In this embodiment, sensor output signals are used instead of a "processed frequency waveform signature" or a structural acoustic signature library as the point of comparison. Although this involves less precision in the categorization of transient load, it improves the ease of processing the detected signals when precise measurement of the nature of the transient load are not desired.

In another embodiment, the method could include detecting the sound generated by the structural member using, for example, a microphone or other esonic devices, to detect airborne sounds which are unrelated to sounds generated by a structural member in good condition in response to a transient load, for example, sounds created by one portion of the structural member rubbing against another portion which sounds are indicative of fractures, cracks, frozen expansion joints, or loosening of components of the structure of which the structural member is a component.

Referring to FIGS. 1 and 12, the present invention also provides for methods of obtaining real time signals from selected transducers secured to a structural members using the real time data at local port 26 of remote electronic unit 820 using portable analysis equipment or signal recording devices, or of obtaining signature samples temporarily stored in signature analysis module 890 taken from selected transducers for transmission to central monitoring station 30 via telemetry port 27. This permits more sophisticated analyses of the signals by, for example, application of conventional pattern recognition techniques or algorithms, for example, the decision-theoretic (or statistical approach, or, more preferably, the syntactic (or linguistic) approach for solving pattern recognition problems, as such appropriate are described in K. S. Fu, Ed., *Pattern Recognition & Machine Learning*, (Plenum Press 1971) and other texts. These latter techniques permit estimating the amount and type of the transient loads applied to a structural member based upon the analysis of the motion of the structural member in response to that load and the sounds created by the transient.

In one embodiment, that method comprises:
(a) detecting the sounds present in and determining a structural acoustic signature of the structural member along a first dimension in response to a transient load at frequencies including the fundamental and harmonic frequencies of the structural member;
(b) providing a library having a plurality of structural acoustic signatures corresponding to the sounds transmitted by the structural member in response to each of a plurality of transient loads subsequent to the duration of the transient load including the fundamental and harmonic frequencies, each of the plurality of loads having a different mass within a range of masses;
(c) determining the structural acoustic signature of the structural member in response to an unknown transient load including a determined fundamental and harmonic frequencies; and
(d) determining the mass of the unknown transient load by selecting from the library the structural acoustic signature of the structural member in response to a known load that is the closest match to the determined signature of the unknown transient load.

In a preferred embodiment, the above method further includes determining the number of harmonic frequencies in the determined structural acoustic signature of the structural member in response to the unknown transient load and selecting from the library a structural acoustic signature of the structural member in response to a transient load of a known mass having the closest number of harmonics, whereby the mass of the unknown transient load is estimated to be the same as the mass of the known transient load.

In another embodiment, the foregoing method step (d) includes using interpolation techniques to determine the mass using the closest match structural acoustic signature of a known mass and the determined fundamental and harmonic frequencies to estimate the unknown mass.

In one preferred embodiment, the foregoing method of step (d) further includes:
(e) detecting the maximum displacement of the structural member during the application of an unknown transient load;
(f) determining the mass of the unknown load from the determined maximum displacement of the structural member during the application of the transient load; and
(g) confirming the determination of the unknown mass by correlating the mass estimated by comparison to the waveform signature library and the mass determined using the maximum displacement of the structural member.

Auto correlation and cross correlation techniques may be used.

In an alternate embodiment, the foregoing method may comprise, in addition to step (a) above:
(b) determining a first structural acoustic signature of the structural member in response to an unknown transient load including a determined fundamental and harmonic frequencies;
(c) comparing the determined first structural acoustic signature to a plurality of threshold signals corresponding to a plurality of categories of signatures, each of said categories corresponding to a range of masses of transient loads, each category having a different range of masses; and
(d) determining the mass of the unknown transient load by selecting the category of the transient loads corresponding to the thresholds for the determined first structural acoustic signature.

The present invention also provides for a method of counting transient loads applied to a structural member. That method includes:
(a) detecting the sound transmitted by the structural member along a first selected dimension by a sensor means for detecting the motion of the structural member in response to a transient load within a frequency range including the natural fundamental and harmonic frequencies of the structural member;
(b) determining a first transient load being applied to the structure from the detected signals subsequent to a transient load including a first fundamental and harmonic frequencies corresponding to the natural fundamental and harmonic frequencies of the structural member;
(c) determining subsequent impacts being applied to the structure from the detected signals during a transient load including a second fundamental and harmonic frequencies of the forced function of the structural member and the transient load; and
(d) counting changes in the detected fundamental and harmonic frequencies corresponding to changes between first fundamental and harmonic frequencies and the second fundamental and harmonic frequencies corresponding to the end of the transient loading of the structural member to count the number of transient loads.

In one embodiment, the method of counting further includes identifying further changes in the detected fundamental and harmonic frequencies corresponding to the response of the structural member to simultaneous or overlapping transient loads as the instantaneous forced function of the structural member and loads changes and counting the changes to count the number of transient loads.

In the application of monitoring bridge structures in accordance with the present invention, a method for determining the velocity of a transient load is provided. That method relies upon the known relationship between the shape of the detected waveform, the mass of the transient load, and the duration that the transient load is in contact with the structural member and the dimensions of the structural member. That method includes:
(a) detecting the sound transmitted by the structural member along a first selected dimension in response to a transient load;
(b) analyzing the detected sound waveform shape including determining the amplitudes of the dundamental and harmonic frequencies;
(c) providing a waveform library having a plurality of defined waveform shapes corresponding to the sound transmitted by the structural member along the first dimension in response to each of a plurality of transient loads during and subsequent to the duration of the transient load, each transient load being applied for a different duration within a range of durations;
(d) subjecting the structural member to an unknown transient load;
(e) detecting the waveform shape of the structural member in response to the unknown transient force including determined amplitudes of the fundamental and harmonic frequencies; and
(f) determining the duration of the unknown transient load by selecting from the waveform shape library the waveform of the structural member in response to a known transient load duration having amplitudes of the fundamental and harmonic frequencies that is the closest match to the amplitudes of the determined waveform of the unknown transient load.

In a preferred embodiment, the method of detecting duration includes determining the speed of a vehicle traveling over the support member of a bridge span whereby the waveform shape library is provided by driving a vehicle over the support member of the span at different rates of speed. The velocity of the transient mass can be determined from the relative displacement of the support member as the transient mass passes the transducer device. How long the displacement exists is indicative of the velocity regardless of the resulting vibrations determinable from the amplitude of the detected waveform signature. A plurality of transducers for detecting sound and interpolation techniques may be used to enhance the accuracy of the determined speed as discussed elsewhere herein.

In an alternate embodiment, the method also may include providing a waveform shape library by subjecting the structural member to known transient loads of different mass as well as different durations or velocities so that identification of an unknown mass can be made more accurate by comparing the detected waveform shape by matching its shape to a shape in the waveform shape library corresponding to the waveform signature of the structural member in response to a known transient load and thereby determining the mass and velocity of the unknown transient load by the known transient load characteristics.

It is to be understood that in each of the foregoing embodiments, the use of a library of data corresponding to known transient loads may be replaced with comparators having threshold values corresponding to the ranges of categories of parameters being measured, e.g., mass, duration or velocity, or both. Thus, detected signals or signatures of a structural member in response to an unknown transient load can be identified by comparison to one or more windows defined by the threshold values of the comparators. The threshold signals selected are typically based on the results of tests performed on a selected test structural member using known loads at known speeds to establish the desired boundaries and scope of the categories to be used. The threshold values may then be adjusted, if necessary, to account for differences between the selected test structural member and the structural member to be monitored, if any, and for changes in the weather or the environment of the structural as neccesary.

The various aspects of the present invention may be combined in any of several combinations to form powerful tools for measuring and analyzing a structural member subjected to transient loads.

Advantageously, the present invention provides for monitoring and analyzing changes in the sound transmission frequency response of a structural member in response to individual, concurrent and successive transient loads using relatively simple, inexpensive, and commercially available or easily fabricated transducer devices and signal processing equipment.

A plurality of transducers for detecting the sound transmitted by a structural member or the displacement of the member may be used and correlation or autocorrelation techniques may be used to enhance the accuracy of the measurements being made. Maintenance programs utilizing the present invention can improve the efficiency of manual inspection by identifying potential problems and setting priorities for inspection, as contrasted with currently existing random or fixed period inspection programs.

In the context of one preferred embodiment of the foregoing aspects, that pertaining to bridge support beams, the invention provides for identifying defects in the support member of the bridge span, counting the number of vehicles passing over the bridge, determining the speed of the passing vehicles, determining the weight category of vehicles, counting and separating by weight the number of large vehicles in a stream of vehicles, and identifying potentially overweight vehicles.

Further aspects allow, for example, for signals to institute marking vehicles identified as potentially overweight or travelling at excessive speeds by photographing license plates, by marking such vehicles with appropriate tag means, alerting appropriate authorities of potentially overweight or speeding vehicles, or some combination of the above. Importantly, the ability to weigh reliably vehicles as they travel with traffic, and particularly heavily congested traffic over bridge spans will provide a considerable economic advantage for highway authorities that are too understaffed to monitor traffic flow or to staff existing roadside scales and advantage the trucking industry in avoiding long lines and idling vehicles while trucks are waiting to be weighed.

It also is believed that once a typical structural member known has been identified by the application of transient loads at different masses at different velocities or durations to create a comprehensive waveform and/or structural acoustic signature library or a series of threshold signals corresponding to the boundaries of desired categories of parameters of transient loads, then other like structures can be more easily calibrated by using a few selected transient loads and adjusting or calibrating the entire waveform signature library or threshold signals according to the results of the few test transient loads. This is particularly true for components of similar size, mass, composition, and configuration, particularly, for example, steel I-beams used in highway bridge construction. Thus, adjustments can be made for environmental differences, for example, different surface treatments of the bridge span, different techniques of securing the support beam in its position, and different weather conditions. This "library" development technique will provide for a cost effective implementation of this invention for monitoring and evaluating a wide variety and large number of structural members for their intended safe use.

One skilled in the art will appreciate that the present invention can be practiced by other than the described embodiments, which are presented for purposes of illustration and not of limitation, and the present invention is limited only by the claims which follow.

We claim:

1. Apparatus for detecting changes in the structural integrity of a structural member comprising:
   (a) linear motion transducer means for detecting the sonic and infrasonic sounds transmitted by the structural member in a first linear dimension in response to a transient load as a time domain signal;
   (b) means for converting the time domain signal into a frequency domain signal;
   (c) means for comparing a first frequency domain signal corresponding to the sonic and infrasonic sounds transmitted by the structural member in said first dimension in response to a first transient load and a second frequency domain signal corresponding to the sonic and infrasonic sounds transmitted by the structural member in said first dimension in response to a second transient load; and
   (d) means for determining that the second frequency domain signal is different than the first frequency domain signal by more than a predetermined amount, said difference corresponding to a change in structural integrity.

2. The apparatus of claim 1, wherein the linear motion transducer means for detecting the sonic and infrasonic sounds generated in the structural member in response to a transient load further comprises an accelerometer.

3. The apparatus of claim 1, further comprising means for detecting motion of the structural member in response to a transient load, said means being a seismic accelerometer for measuring the displacement of the structural element during the application of a transient load.

4. The apparatus of claim 3, further comprising a means for detecting abnormal displacement conditions of the structural member.

5. The apparatus of claim 1, further comprising:
   (e) means for providing a library including a plurality of frequency domain signals corresponding to the detected sonic and infrasonic sounds in response to a corresponding plurality of transient loads of known mass under a plurality of weather conditions; and
   (f) means for comparing a detected frequency domain signal to the frequency domain signals in the library to determine whether the detected signal corresponds to any of the frequency domain signals in the library within a predetermined amount.

6. The apparatus of claim 1 wherein the detected sonic and infrasonic sounds include the fundamental and harmonic frequencies of the structural member, wherein step (c) further comprises comparing the higher order harmonic frequencies of the first frequency domain signal to the higher order harmonic frequencies of the second frequency domain signal, and wherein step (d) further comprises determining that the second frequency domain signal is different than the first frequency domain signal by more than a predetermined amount based upon the differences in the higher order harmonic frequencies.

7. A method of detecting changes in the structural integrity of a structural member comprising:
   (a) detecting the sound transmitted by the structural member along a first linear dimension in response to a transient load at frequencies including the natural fundamental and harmonic frequencies of the structural member along the first linear dimension; and
   (b) subjecting the structural member to a first transient load; and
   (c) determining a first structural acoustic signature from the detected sounds transmitted along the first linear dimension by the structural member in response to the first transient load, said first signature including the detected fundamental and harmonic frequencies subsequent to the first transient load; and thereafter
   (d) subjecting the structural member to a second transient load;
   (e) determining a second structural acoustic signature from the detected sound transmitted along the first linear dimension by the structural member in response to the second transient load, said second signature including the detected fundamental and harmonic frequencies subsequent to the second transient load; and
   (f) comparing the second signature and the first signature to determine whether the detected fundamental or harmonic frequencies of the first signature and the second signatures differ by more than a predetermined amount, whereby any such difference corresponds to a change in structural integrity.

8. The method of claim 7 wherein the predetermined amount is selected to correspond to changes in elasticity of the structural member that result from changes in the environmental conditions and not changes in structural integrity.

9. The method of claim 7 wherein detecting the sounds transmitted by the structural member along a first linear dimension further comprises detecting sonic and infrasonic frequencies.

10. The method of claim 9 wherein detecting the sounds transmitted further comprises measurement he acceleration of the structural member along the first linear dimension.

11. The method of claim 9 further comprising detecting the sonic and infrasonic frequencies transmitted by the structural member along a second linear dimension in response to a transient load; and
    following each of steps (b)-(e) to detect the sounds transmitted by the structural member in response to the first and second transient loads in the second linear dimension, thereby determining a first and a second structural acoustic signature in the second linear dimension;
    comparing the second signature in the second linear dimension to the first signature in the second linear dimension to determine whether the detected fundamental or harmonic frequencies of the first and the second signatures in the second linear dimension differ by more than a second predetermined amount, whereby any such difference corresponds to a change in structural integrity in the second linear dimension;
    correlating the determination of whether there was a difference in the first and second signatures in the first linear dimension with the determination of whether there was a corresponding difference in the first and second signatures in the second linear dimension; and
    determining whether there has been a change in structural integrity using the determinations of differences in the first and second signatures in the first and second linear dimensions and the determined correlation.

12. The method of claim 11 wherein the first dimension and second dimension are perpendicular to each other.

13. The method of claim 9 wherein said first linear dimension further comprises a second linear dimension and a third linear dimension and said method steps (a), (c), and (e) further comprise detecting said sonic and infrasonic frequencies transmitted by the structural member in said second and third linear dimensions in response to a first transient load, determining said first structural acoustic signature from the detected sonic and infrasonic frequencies transmitted along the second and third linear dimensions by the structural member in response to the first transient load, and determining a second structural acoustic signature from the detected sonic and infrasonic frequencies transmitted along said second and third linear dimensions by the structural member in response to the second transient load.

14. The method of claim 13 wherein the second linear dimension and the third linear dimension are perpendicular to each other.

15. The method of claim 7 wherein the structural member further comprises a support beam for a bridge span and wherein detecting the sounds transmitted in the first dimension further comprises detecting the frequencies in the longitudinal dimension within the range of from about 0.1 Hz to about 20 kHz.

16. The method of claim 15 wherein detecting the sounds transmitted by the structural member in response to a transient load further comprises detecting the sounds transmitted along a longitudinal, a vertical, and a lateral dimension of the structural member, wherein determining a first and second structural acoustic signature in response to the first and second transient loads further comprise determining a first signature in each of the longitudinal, vertical, and lateral dimensions, determining a second signature in each of the longitudinal, vertical, and lateral dimensions, and wherein comparing the first and second signatures further comprises comparing each of the longitudinal, vertical, and lateral first signatures to the corresponding respective second signatures to determine changes in the fundamental or harmonic frequencies in the vertical, longitudinal, or lateral dimension signatures corresponding to changes in structural integrity.

17. The method of claim 7 wherein comparing the second signature to the first signature further comprises identifying a change in structural integrity as a localized defect in the structural member by identifying in the second signature a new fundamental or harmonic frequency at a frequency or amplitude that does not exist in the first signature.

18. The method of claim 17 further comprising identifying the relative location of a detected localized defect in the structural member by determining the wavelength of the new fundamental or harmonic frequency or amplitude of the second signature and correlating said wavelength to the dimension along which the sounds of the second signature were detected so as to determine the distance from one end of the structural member to said localized defect.

19. The method of claim 7 wherein comparing the second signature to the first signature further comprises identifying a determined change in structural integrity as a change in stiffness of the structural member by identifying a shift in the detected natural fundamental or harmonic frequencies in the second signature relative to the first signature.

20. The method of claim 7 wherein said first signature further comprises a reference signature corresponding to sounds transmitted by the structural member in response to the first transient load when the structural member is determined to be in good condition, and wherein said second signature further comprises a determined signature corresponding to the sounds transmitted by the structural member in response to a transient load occurring subsequent to the first transient load.

21. The method of claim 7 wherein said second signature becomes the first signature and the detected sounds transmitted by the structural member in response to a third transient load subsequent to the first and second transient loads becomes the second signature so that each determined signature is compared to a previously occurring determined signature.

22. The method of claim 7 wherein detecting the sounds transmitted by the structural member further comprises detecting the sonic and infrasonic frequencies in a first dimension at a first location on the structural member, the method further comprising:
(g) detecting the sonic and infrasonic sounds transmitted by the structural member along the first dimension in response to a transient load at a second location on the structural member;
(h) determining a third structural acoustic signature corresponding to the detected sounds transmitted by the structural member at the second location in response to the first transient load;
(i) determining a fourth structural acoustic signature corresponding to the detected sounds transmitted by the structural member at the second location in response to the second transient load;
(j) comparing the fourth and third signatures to determine whether there has been a change in structural integrity in step (f);
(k) correlating the determination made in step (f) with the determination made in step (j); and
(l) determining whether there has been a change in structural integrity of the structural member using the determinations made in steps (f) and (j) and the correlation of step (k).

23. The method of claim 7 further comprising:
(g) detecting the airborne sound generated by the structural member in response to a transient load;
(h) determining a first sound waveform corresponding to the detected airborne sound generated by the structural member in response to the first transient load;
(i) determining a second sound waveform corresponding to the detected airborne sound generated by the structural member in response to the second transient load;
(j) comparing the first and second sound waveforms to determine whether there are frequencies occurring in the second sound waveform that do not have corresponding frequencies in the first sound waveform, whereby any such frequencies correspond to changes in structural integrity of the structural member;
(k) correlating the determination made in step (f) with the determination made in step (j); and
(l) determining whether there has been a change in structural integrity of the structural member using the determinations in steps (f) and (j) and the correlation of step (k).

24. An apparatus for detecting changes in the structural integrity of a structural member having a mass and dimension comprising:
(a) linear motion transducer means for detecting the sonic and infrasonic frequencies transmitted by the structural member in a first linear dimension in response to a transient load including the natural fundamental and harmonic frequencies of the structural member;
(b) first processing means for converting the detected frequencies into a structural acoustic signatures in the frequency domain;
(c) second processing means for comparing a first structural acoustic signature corresponding to the frequencies transmitted by the structural member in said first dimension in response to a first transient load to a second structural acoustic signature corresponding to the frequencies transmitted by the structural member in said first dimension in response to a second transient load; and
(d) means for determining that the structural integrity of the structural member has changed when the portion of the second signature corresponding to the second transient load differs from the portions of the first signature by more than a predetermined amount.

25. The apparatus of claim 24 wherein said linear motion transducer means further comprises means for detecting displacement and acceleration of said transient member.

26. The apparatus of claim 25 wherein said means for detecting displacement and acceleration of said transient member further comprises an accelerometer.

27. The apparatus of claim 24 wherein said linear motion transducer means detects sounds transmitted along more than one direction of the structural member.

28. The apparatus of claim 27 further comprising means for correlating the determined changes in structural integrity in each of said directions of the structural member and means for confirming the determination using the determined correlation and the determined changes for each direction.

29. The apparatus of claim 24 wherein said first processing means further comprises means for using Fourier transforms to convert the detected frequencies into the frequency domain signals.

30. The apparatus of claim 24 further comprising alarm means for indicating that there is a determined change in structural integrity of the structural member.

31. The apparatus of claim 24 wherein said second processing means and said means for determining further comprise means for identifying a determined change in structural integrity as a change in stiffness of the structural member by identifying a shift in the detected natural fundamental or harmonic frequencies in the second signature relative to the first signatures.

32. The apparatus of claim 24 wherein said second processing means and said means for determining further comprise means for identifying a determined change in structural integrity as a localized defect in the structural member by identifying in the second signature a new fundmantal or harmonic frequency at a frequency or amplitude that does not exist in the first signature.

33. The apparatus of claim 32 further comprising means for identifying the relative location of a detected localized defect in the structural member by determining the wavelength of the new fundamental or harmonic frequency or amplitude of the second signature and means for correlating the said wavelength to the dimension of the structural member along which the sound of the second signature was detected so as to determine the distance from one end of the structural member to said localized defect.

34. An apparatus for detecting changes in the structural integrity of a structural member having a mass and dimension comprising:
  (a) a triaxial accelerometer for detecting the sonic and infrasonic frequencies transmitted by the structural member along more than one direction of the structural member in response to a transient load including the natural fundamental and harmonic frequencies of the structural member;
  (b) first processing means for converting the detected frequencies into a structural acoustic signature in the frequency domain;
  (c) second processing means for comparing a first structural acoustic signature corresponding to the frequencies transmitted by the structural member in response to a first transient load to a second structural acoustic signature corresponding to the frequencies transmitted by the structural member in response to a second transient load; and
  (d) means for determining that the structural integrity of the structural member has changed when the portion of the second signature corresponding to the second transient load differs from the portion of the first signature by more than a predetermined amount.

35. An apparatus for detecting changes in the structural integrity of a structural member having a mass and dimension comprising:
  (a) transducer means for detecting the sonic and infrasonic frequencies transmitted by the structural member by detecting the displacement and acceleration of the transient member in response to a transient load including the natural fundamental and harmonic frequencies of the structural member;
  (b) an esonic transducer device for detecting the airborne sounds generating by the structural member in response to the transient load;
  (c) first processing means for converting the detected frequencies into a structural acoustic signature in the frequency domain;
  (d) second processing means for comparing a first structural acoustic signature corresponding to the frequencies transmitted by the structural member in response to a first transient load to a second structural acoustic signature corresponding to the frequencies transmitted by the structural member in response to a second transient load;
  (e) third processing means for comparing a first esonic signal corresponding to the detected airborne sounds generated by the structural member in response to a first transient load to a second esonic signal corresponding to the detected airborne sounds generated by the structural member in response to a second transient load; and
  (f) means for determining that the structural integrity of the structural member has changed when the portion of the second signature corresponding to the second transient load differs from the portion of the first signature by more than a predetermined amount and the first and second esonic signals contain different frequencies.

* * * * *